United States Patent
Bohm et al.

(10) Patent No.: US 12,089,933 B2
(45) Date of Patent: *Sep. 17, 2024

(54) SENSORS FOR CONTINUOUS ANALYTE MONITORING

(71) Applicant: DexCom, Inc., San Diego, CA (US)

(72) Inventors: Sebastian Bohm, San Diego, CA (US); Pradnya Prakash Samant, Atlanta, GA (US); Jiong Zou, San Diego, CA (US)

(73) Assignee: DEXCOM, INC., San Diego, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 17/895,755

(22) Filed: Aug. 25, 2022

(65) Prior Publication Data

US 2022/0409138 A1    Dec. 29, 2022

Related U.S. Application Data

(63) Continuation of application No. 15/872,280, filed on Jan. 16, 2018, now Pat. No. 11,457,870.

(60) Provisional application No. 62/447,822, filed on Jan. 18, 2017.

(51) Int. Cl.
  *A61B 5/1486* (2006.01)
  *A61B 5/00* (2006.01)
  *A61B 5/145* (2006.01)

(52) U.S. Cl.
  CPC ...... *A61B 5/14865* (2013.01); *A61B 5/14532* (2013.01); *A61B 5/6848* (2013.01)

(58) Field of Classification Search
  CPC .............. A61B 5/14507; A61B 5/1451; A61B 5/14532; A61B 5/14546; A61B 5/1473–14735; A61B 5/1486–14865
  See application file for complete search history.

(56) References Cited

U.S. PATENT DOCUMENTS

| | | |
|---|---|---|
| 8,886,273 B2 | 11/2014 | Li et al. |
| 9,241,651 B2 | 1/2016 | Fedder et al. |
| 11,457,870 B2 * | 10/2022 | Bohm ............... A61B 5/14532 |
| 2002/0072720 A1 | 6/2002 | Hague et al. |
| 2004/0202719 A1 | 10/2004 | Zion et al. |
| 2009/0143659 A1 | 6/2009 | Li et al. |
| 2011/0073475 A1 | 3/2011 | Kastanos et al. |
| 2012/0046533 A1 | 2/2012 | Voskanyan et al. |
| 2013/0131482 A1 | 5/2013 | Fedder et al. |
| 2013/0197332 A1 | 8/2013 | Lucisano et al. |
| 2015/0289788 A1 * | 10/2015 | Simpson ............ A61B 5/14532 |
| | | 225/2 |
| 2016/0338734 A1 | 11/2016 | Shah et al. |

(Continued)

FOREIGN PATENT DOCUMENTS

WO    2015156966 A1    10/2015

OTHER PUBLICATIONS

International Bureau of WIPO; International Preliminary Report on Patentability for Application No. PCT/US2018/013821 mailed Aug. 1, 2019, 11 pages.

(Continued)

*Primary Examiner* — Meredith Weare
(74) *Attorney, Agent, or Firm* — Moore & Van Allen PLLC

(57) ABSTRACT

Sensor devices including dissolvable tissue-piercing tips are provided. Methods of using and fabricating sensor devices are also provided.

20 Claims, 33 Drawing Sheets

(56) References Cited

U.S. PATENT DOCUMENTS

2017/0028184 A1    2/2017   Godden et al.
2017/0348218 A1* 12/2017   Chen .................... A61K 8/735
2018/0199886 A1    7/2018   Bohm et al.

OTHER PUBLICATIONS

USPTO; International Search Report and Written Opinion for Application No. PCT/US2018/013821 mailed May 7, 2018, 12 pages.

* cited by examiner

Diameter - 270±50 μm
Height - 470±50 μm

SENSORS FOR CONTINUOUS ANALYTE MONITORING

CROSS-REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/872,280, filed Jan. 16, 2018, which claims the benefit of U.S. Provisional Application No. 62/447,822, filed Jan. 18, 2017. The aforementioned applications are incorporated by reference herein in their entireties, and is hereby expressly made a part of this specification.

FIELD

The subject matter disclosed herein relates to systems and methods for measuring an analyte concentration in a host.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements associated with the deterioration of small blood vessels, for example, kidney failure, skin ulcers, or bleeding into the vitreous of the eye. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricks to obtain blood samples for measurement. Due to the lack of comfort and convenience associated with finger pricks, a person with diabetes normally only measures his or her glucose levels two to four times per day. Unfortunately, time intervals between measurements may be spread far enough apart that the person with diabetes finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional methods. Diabetics thus may be inhibited from making educated insulin therapy decisions.

Another device that some diabetics use to monitor their blood glucose is a continuous analyte sensor. A continuous analyte sensor typically includes a sensor that is placed subcutaneously, transdermally (e.g., transcutaneously), or intravascularly. The sensor measures the concentration of a given analyte within the body, and generates a raw signal that is transmitted to electronics associated with the sensor. The raw signal is converted into an output value that is displayed on a display. The output value that results from the conversion of the raw signal is typically expressed in a form that provides the user with meaningful information, such as blood glucose expressed in mg/dL.

SUMMARY

The various present embodiments have several features, no single one of which is solely responsible for their desirable attributes. Without limiting the scope of the present embodiments as expressed by the claims that follow, their more prominent features now will be discussed. After considering this discussion, and particularly after reading the section entitled "Detailed Description," one will understand how the features of the present embodiments provide the advantages described herein.

One aspect of the present embodiments includes the realization that tack sensors include a sharpened tip that remains implanted in the tissue throughout the usable life of the sensor. Leaving the sharpened tip in vivo for an extended period of time may cause trauma to surrounding tissue, leading to scarring and inhibition of wound healing. Another aspect of the present embodiments includes the realization that in some current methods for sensor insertion the sensor is received within the lumen of an insertion needle. The needle, which has greater column strength than the sensor, bears the frictional forces that occur during insertion. Once the sensor is in place in the tissue, the needle is removed. The need to remove the needle adds complexity to the insertion process, including the need to electrically connect the sensor to sensor electronics after insertion. Some of the present embodiments provide solutions to these problems.

In recognition of the foregoing problems, a first aspect of the present embodiments comprises a sensor device for measuring an analyte concentration in a host, the sensor device comprising: a sensor unit comprising a sensor body, at least one electrode, and a membrane covering at least a portion of the at least one electrode, the sensor body having a blunt tip; a piercing element comprising a material that dissolves upon insertion into the host, the piercing element abutting the sensor tip and being capable of piercing tissue; and a mounting unit spaced from the sensor tip and configured to support the sensor device on an exterior surface of the host's skin. Further disclosed is reinforced sensor wire, comprising a sensor wire and a coating comprising a dissolvable material, wherein the reinforced sensor has a buckling force of greater than 0.04 lbf.

Also in recognition of the foregoing problem, a second aspect of the present embodiments comprises a method of making a sensor device, the method comprising dipping at least a tip of a sensor into a liquid to form a coating of the liquid on the sensor tip; and withdrawing the sensor tip from the liquid while controlling parameters of the withdrawal so that the coating forms a tissue-piercing element extending from the sensor tip, wherein the coating comprises a dissolvable material that dissolves upon insertion into the host.

Also a third aspect of the present embodiments comprises a method of making a sensor device, the method comprising, in any order, inserting at least a tip of a sensor into a mold; adding a liquid to the mold; and separating the sensor from the mold when the liquid has dried and formed a tissue-piercing element extending from the sensor tip, wherein the coating comprises a dissolvable material that dissolves upon insertion into the host.

In an embodiment of the first, second, or third aspects, the sensory body can be coated with a sheath and the sheath comprises the dissolvable material.

In an embodiment of the first, second, or third aspects, the dissolvable material can have a rate of dissolution in phosphate buffer solution from about 20 mg/min to about 60 mg/min.

In an embodiment of the first, second, or third aspects, the dissolvable material can have a tensile strength of from about 20 MPa to about 90 MPa.

In an embodiment of the first, second, or third aspects, the dissolvable material can have a Young's modulus of from about 1 GPa to about 10 GPa.

In an embodiment of the first, second, or third aspects, the dissolvable material can comprise two or more water soluble polymers.

In an embodiment of the first, second, or third aspects, the tissue-piercing element can have an aspect ratio of from about 0.5 to about 7.

In an embodiment of the first, second, or third aspects, the tissue-piercing element can have a base diameter $D_{tip}$ and the sensor body has a diameter $D_{wire}$, and the ratio $D_{tip}/D_{wire}$ is greater than 0.75.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

The following detailed description describes the present embodiments with reference to the figures. In the figures, reference numbers label elements of the present embodiments. These reference numbers are reproduced below in connection with the discussion of the corresponding figures features.

The figures and their descriptions may indicate sizes, shapes and configurations of the various components. Such depictions and descriptions should not be interpreted as limiting. Alternative sizes, shapes and configurations are also contemplated as within the scope of the present embodiments. Also, the figures, and their written descriptions, indicate that certain components of the apparatus are formed integrally, and certain other components are formed as separate pieces. Components shown and described herein as being formed integrally may in alternative embodiments be formed as separate pieces. Further, components shown and described herein as being formed as separate pieces may in alternative embodiments be formed integrally. As used herein the term integral describes a single unitary piece.

Overview

The embodiments described herein provide various mechanisms, materials, and devices for directly inserting a transcutaneous sensor into a host without the use of a separate applicator, i.e., other than the sensor device itself. Direct press insertion of a transcutaneous sensor (e.g., an electrode) having a wire-like geometry, especially a fine wire, may be technically challenging because of buckling risks associated with the sensor. Direct press insertion of a sensor also presents challenges relating to damage during the insertion process to the membrane disposed on the sensor. Without membrane protection, the membrane may be stripped off from the sensor or be mechanically damaged during the insertion process. The embodiments described herein are designed to overcome the aforementioned challenges by providing sensor devices capable of providing structural support (e.g., in the form of mechanical/structural properties such as column strength) for direct insertion of a transcutaneous sensor and capable of protecting the membrane from damage during the insertion process.

Figure 1:
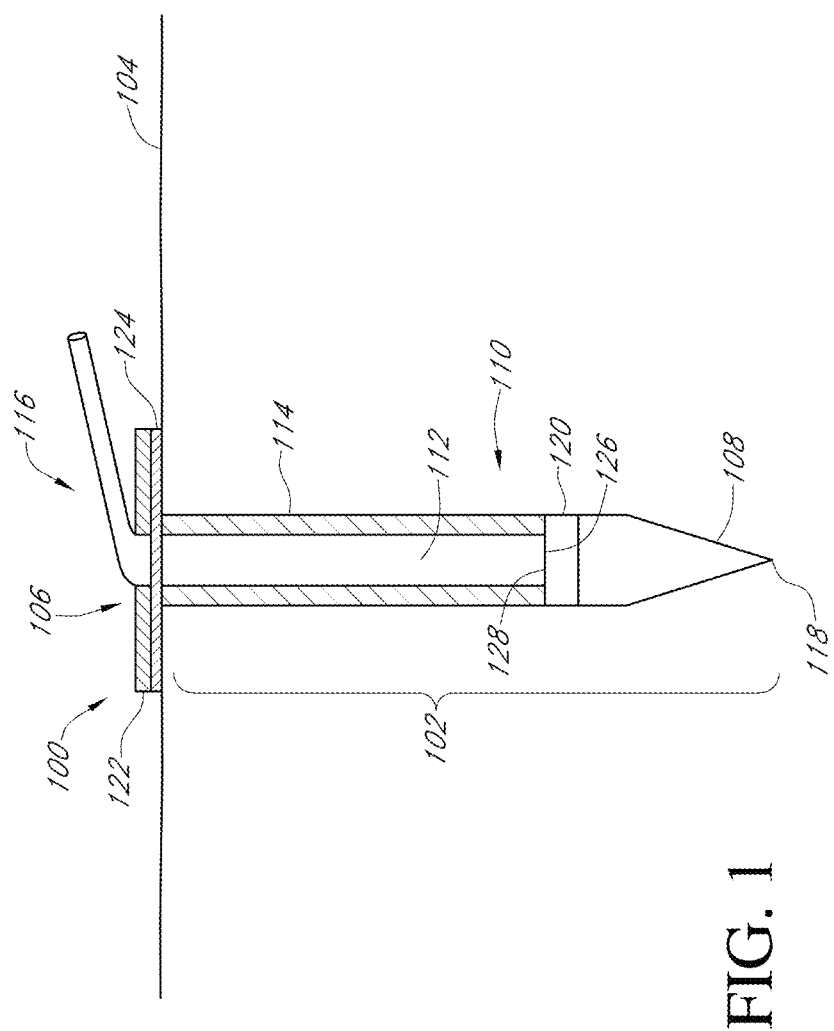
FIG. 1 is a schematic cross-sectional view of a continuous analyte sensor according to the present embodiments.

FIG. 1 illustrates a schematic side view of one embodiment of a transcutaneous sensor device 100 configured to continuously measure analyte concentration (e.g., glucose concentration) in a host to provide a data stream representative of the host's analyte concentration, in accordance with the present embodiments. Sensors such as the one illustrated in FIG. 1 are sometimes referred to as "tack" sensors, due to their resemblance to a thumbtack.

In the particular embodiment illustrated in FIG. 1, the sensor device 100 comprises an in vivo portion 102 (also referred to as a sensor unit) configured for insertion under the host's skin 104, and an ex vivo portion 106 configured to remain above the host's skin surface after sensor insertion. The in vivo portion 102 comprises a tissue-piercing element 108 configured for piercing the host's skin 104, and a sensor body 110. The sensor body 110 comprises a support member 112 including one or more electrodes, and a membrane 114 disposed over at least a portion of the support member 112. The support member 112 may also be referred to as a sensor body 112, and the two terms are used interchangeably herein. The support member 112 can also contain a sensor wire that conducts an analyte signal to the sensor electronics (not shown) or, alternatively, the support member 112 is itself the sensor wire, thus serving the both purposes.

The ex vivo portion 106 comprises a mounting unit 116 that may include a sensor electronics unit (not shown) embedded or detachably secured therein, or alternatively may be configured to operably connect to a separate sensor electronics unit. Further details regarding the sensor device 100 and its components may be found in U.S. Patent Application Publication No. 2011/0077490, the disclosure of which is incorporated herein in its entirety.

Tissue-Piercing Element

The tissue-piercing element 108 of the sensor device 100 is configured to pierce the host's skin 104, and to open and define a passage for insertion of the sensor body 110 into a tissue of the host. In some embodiments, the tissue-piercing element 108 may be integral with the support member 112. In other embodiments, the tissue-piercing element 108 may be a discrete component separate from, for example, the sensor body 112. In such embodiments, the tissue-piercing element 108 may be secured to the support member 112, such as with an adhesive. In such embodiments, the sensor body 112 may include a blunt tip or distal face 126. The tissue-piercing element 108 similarly includes a blunt proximal face 128 that abuts the sensor body tip 126. Alternatively, the tissue-piercing element 108 may merely abut a blunt distal face of the support member 112 and/or the membrane 114. In such embodiments, an outer sleeve or band (not shown) may encircle a junction of the tissue-piercing element 108 and the support member 112/membrane 114.

The skin generally comprises multiple layers, including the epidermis, dermis, and subcutaneous layers. The epidermis comprises a number of layers within its structure including the stratum corneum, which is the outermost layer and is generally from about 10 to 20 microns thick, and the stratum germinativum, which is the deepest layer of the epidermis. While the epidermis generally does not contain blood vessels, it exchanges metabolites by diffusion to and from the dermis. While not wishing to be bound by theory, it is believed that because the stratum germinativum is supported by vascularization for survival, the interstitial fluid at the stratum germinativum sufficiently represents a host's analyte (e.g., glucose) levels. Beneath the epidermis is the dermis, which is from about 1 mm to about 3 mm thick and contains blood vessels, lymphatics, and nerves. The subcutaneous layer lies underneath the dermis and is mostly comprised of fat. The subcutaneous layer serves to insulate the body from temperature extremes. It also contains connective tissue and a small amount of blood vessels.

In some embodiments, the in vivo portion 102 of the sensor device 100 may have a length long enough to allow for at least a portion of the sensor body 110 to reside within the stratum germinativum. This may be desirable in some instances because the epidermis does not contain a substantial number of blood vessels or nerve endings. Thus, sensor insertion may be relatively painless, and the host may not experience much bleeding or discomfort from the insertion.

In some of these embodiments, the in vivo portion 102 of the sensor device 100 may have a length of from about 0.1 mm to about 1.5 mm, or from about 0.2 mm to about 0.5 mm. In other embodiments, the in vivo portion 102 of the sensor device 100 may have a length that allows for at least a portion of the sensor body 110 to reside in the dermis layer. This may be desirable in some instances because the dermis is well vascularized, as compared to the subcutaneous layer, and thus may provide sufficient analytes (e.g., glucose) for measurement and reduce measurement lags associated with changes of analyte concentrations of a host, such as those that occur after meals. The metabolically active tissue near the outer dermis (and also the stratum germinativum) provides rapid equilibrium of the interstitial fluid with blood. In some of these embodiments, the in vivo portion 102 of the sensor device may have a length of from about 1 mm to about 7 mm, or from about 2 mm to about 6 mm. In still other embodiments, the in vivo portion 102 of the sensor device 100 may have a length that allows for at least a portion of the sensor body 110 to reside in the subcutaneous layer. While not wishing to be bound by theory, it is believed that because the subcutaneous layer serves to insulate the body from temperature extremes, the subcutaneous layer may reduce variations of analyte concentration readings associated with temperature fluctuations. In some of these embodiments, the in vivo portion 102 of the sensor device may have a length of from about 3 mm to about 10 mm, or from about 5 mm to about 7 mm.

Figure 2A:
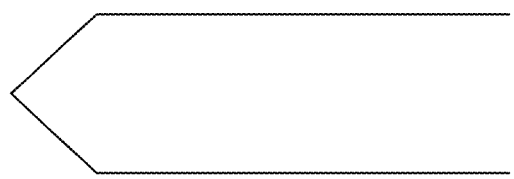
FIGS. 2A-2H are schematic side views of example shapes of tissue-piercing tips for a continuous analyte sensor according to the present embodiments.
Figure 2B:
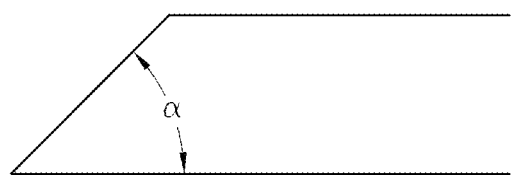
Figure 2C:
Figure 2D:
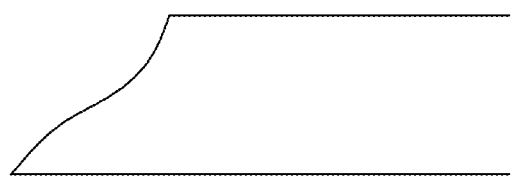
Figure 2E:
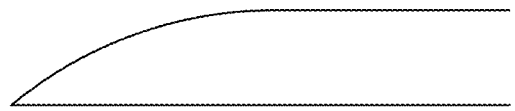
Figure 2F:
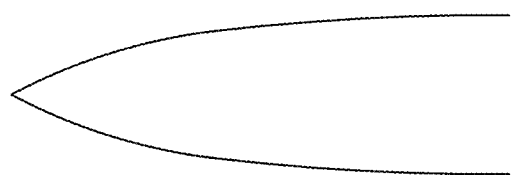
Figure 2G:
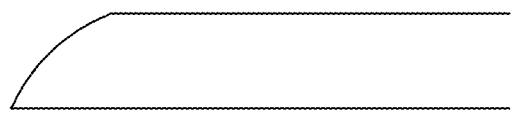
Figure 2H:

The tissue-piercing element may have any of a variety of geometric shapes and dimensions, including ones that minimize tissue trauma and reduce the force required for skin penetration. For example, in some embodiments, the tissue-piercing element may comprise a substantially conically-shaped distal tip, as illustrated in FIG. 1, such that the cross-sectional dimensions (e.g., diameter) of the tissue-piercing element tapers to a point 118 at the distal end of the tip, thereby providing a sharpened leading edge configured to facilitate skin penetration. As illustrated in FIG. 2B, in other embodiments, the distal tip of the tissue-piercing element may be beveled with a bevel angle α, such as, for example, an angle of from about 5° to about 66°, or from about 10° to about 55°, or from about 40° to about 50°. In further embodiments, one or more surfaces of the tip may be curved, such as illustrated in FIGS. 2C-2H and 3D, so as to facilitate skin penetration when the sensor device is pushed downwards. In some embodiments, a curved surface may be advantageous because it provides the tissue-piercing element with a greater cutting surface area than a straight surface, and thus provides a smoother and more controlled insertion of the sensor unit through the skin. Also, a tissue-piercing element with a curved surface may cause less trauma to the pierced tissue than one with a straight surface.

The tissue-piercing element of the sensor device is designed to have appropriate flexibility and hardness and sufficient column strength to prevent it from substantial buckling during insertion of the in vivo portion of the sensor device through the skin of the host. In certain embodiments, the tissue-piercing element has sufficient column strength to allow the user to press the sensor unit through the skin using the force from a thumb or finger, without substantial buckling of the tissue-piercing element. Accordingly, the structure of the tissue-piercing unit does not fail when it is subjected to resistance (e.g., axial force) associated with the penetration of tissue and skin. In some embodiments, the tissue-piercing element may have a column strength capable of withstanding an axial load greater than about 0.5 Newtons, or greater than about 1 Newton, or greater than about 2 Newtons, or greater than about 5 Newtons, or greater than about 10 Newtons, without substantial buckling. Often, an increase in the column thickness of an object will also increase its column strength. In some embodiments, the base 120 of the distal tip may have an outside diameter of from about 0.05 mm to about 1 mm, or from about 0.1 mm to about 0.5 mm, or from about 0.15 mm to about 0.3 mm, to provide the desired column strength for the tissue-piercing element.

In other embodiments, tissue-piercing element can be from about 200 μm to about 1000 μm in length, e.g., from about 300 μm to about 900 μm, from about 400 μm to about 800 μm, from about 500 μm to about 700 μm, from about 200 μm to about 500 μm, or from about 500 μm to about 800 μm in length. The diameter of the tissue piercing element at its base where it abuts the sensor wire, its widest point, can be from about 100 μm to about 500 μm, e.g., from about 200 μm to about 400 μm, from about 100 μm to about 200 μm, from about 200 μm to about 300 μm, or from about 300 μm to about 500 μm. The size of the tissue-piercing element can also be characterized by an aspect ratio. The aspect ratio is defined as the tip height, which is the distance from the base to the tip of the tissue piercing element, divided by the diameter of the tissue piercing element at its base, where it abuts against the sensor body. In some embodiments, the aspect ratio of the tissue-piercing element can be from about 0.5 to about 7, e.g., about 1, 1.5, 2, 2.5, 3, 3.5, 4, 4.5, 5, 5.5, 6, 6.5, or 7, where any of the stated values can form an upper or lower endpoint of a range.

The diameter of the tissue-piercing element at its base where it abuts the sensor wire ($D_{tip}$) should be within 25% of the diameter of the sensor wire ($D_{wire}$). Thus, $D_{tip}/D_{wire}$ ratio should be greater than 0.75, e.g., 0.8, 0.85, 0.9, 0.95, 1.0, 1.05, 1.1, 1.15, where any of the stated values can form an upper or lower endpoint of a range.

Some of the tissue-piercing elements described herein are configured to protect the membrane of the sensor body. As described elsewhere herein, the membrane may be relatively delicate, and thus may be damaged during insertion of the sensor unit into the host. Consequently, any damage sustained by the membrane may affect the sensor device's performance and its ability to function properly. For example, in some embodiments one or more portions of the tissue-piercing element 108 may be formed with a cross-sectional area (along a plane transverse to the longitudinal axis of the tissue-piercing element 108) larger than that of the sensor body 110. By having a cross-sectional area larger than that of the sensor body 110, the tissue-piercing element 108 of the sensor device 100 is configured to pierce the host's skin 104 and to open and define a passage for insertion of the sensor body 110 into the tissue. In other embodiments, the tissue-piercing element may conform to the wire base and have a diameter that is within 50% of the diameter of the sensor body. In some embodiments, the tissue-piercing element may conform to the wire base and have a diameter that is within 30% of the diameter of the sensor body. Thus, the risk of a penetration-resistance force damaging and/or stripping the membrane 140 off from the rest of the sensor body 110 during the insertion process is reduced. In some embodiments, the largest dimension of the cross section transverse to a longitudinal axis of the tissue-piercing element 108 is less than about 0.1 mm, or less than about 0.05 mm, or less than about 0.03 mm.

Dissolvable Tip

In the disclosed embodiments, the tissue-piercing element is comprised of materials that dissolve after implantation into the host. These dissolvable materials, as disclosed herein, are distinguishable from materials that degrade over time; degradable materials break down into different compounds. The disclosed dissolvable materials dissolve away, but retain their identity. Also, the dissolvable materials, after they dissolve, leave the membrane unchanged. So the membrane in situ has the same characteristics after the dissolvable material dissolves as it would had there been no dissolvable material on the tip.

A rate of dissolution of the tissue-piercing element depends upon the amount and type of dissolvable material present. In some embodiments, the tissue-piercing element completely dissolves within 3 hours of implantation into the host, e.g., within 2.5 hours, 2 hours, 1.5 hours, 1 hour, 30 minutes, 15 minutes, or 5 minutes of implantation into the host.

In other embodiments, the dissolvable material used in the tissue-piercing element can have a rate of dissolution in phosphate buffer solution from about 20 mg/min to about 60 mg/min, e.g., from about 40 mg/min to about 50 mg/min, from about 30 mg/min to about 50 mg/min, from about 30 mg/min to about 40 mg/min, or from about 50 mg/min to about 60 mg/min. Dissolution rate is determined by placing a dog-bone shaped material of known weight (e.g., from 10 to 100 mg) in phosphate buffer solution under constant agitation and noting the time at which the dog-bone completely dissolves.

In certain embodiments, the material may dissolve within a timeframe before which the sensor begins operating. In such embodiments, the dissolved material of the tissue-piercing element 108 may not interfere with sensor calibration.

In other embodiments, the dissolvable material used in the tissue-piercing element can have a tensile strength of from about 20 MPa to about 90 MPa, e.g., from about 20 MPa to about 70 MPa, from about 20 MPa to about 50 MPa, from about 40 MPa to about 90 MPa, from about 40 MPa to about 70 MPa, or from about 60 MPa to about 90 MPa. Tensile strength is measured using method ASTM-D2370.

In other embodiments, the dissolvable material used in the tissue-piercing element can have a Young's modulus of from about 1 GPa to about 20 GPa. In some embodiments, the Young's Modules is from about 1 GPa to about 10 GPa, and preferably from about 1 GPa to about 5 GPa. Young's modulus is measured using method ASTM-D2370.

The dissolvable material of tissue-piercing element can be comprised of a combination of water-soluble, natural or synthetic polymers, proteins, or polysaccharides. By varying the type and amount of the compounds, the properties of dissolution rate, rigidity, and strength can be achieved. In certain embodiments, the dissolvable material can comprise a combination of water soluble polymers with an optional binder.

In certain embodiments, the dissolvable materials comprise one or more of a polyvinylalcohol, polyvinylpyrrolidone, protein, or polysaccharide. It is also contemplated that derivatives and blends of these polymers can be used as well. These materials can be chosen based on their biocompatibility, strength, stiffness, and binding characteristics. Moreover, since no single material can confer all the required properties to the tip, it is helpful to use a combination of these materials in the final formulation to make the dissolvable material for the tissue-piercing element. To identify exemplary formulations, the strength and stiffness of the different combinations can be tested.

PVA

In specific embodiments, the dissolvable material of the tissue-piercing element can comprise polyvinyl alcohol or polyvinyl alcohol-co-vinyl acetate (PVA). PVA is a biocompatible, inert polymer with beneficial lubricating and binding properties. It has high strength and strong adhesion. The PVA can have a degree of saponification of at least about 50%, e.g., at least about 60%, at least about 70%, at least about 80%, at least about 90%, or at least about 99%. The PVA can also have a MW of from about 5,000 Da to about 75,000 Da, e.g., from about 5,000 Da to about 50,000 Da, from about 5,000 Da to about 25,000 Da, from about 10,000 Da to about 75,000 Da, from about 10,000 Da to about 25,000 Da, from about 25,000 Da to about 50,000 Da, from about 20,000 Da to about 75,000 Da, from about 20,000 Da to about 50,000 Da, from about 30,000 Da to about 75,000 Da, from about 30,000 Da to about 50,000 Da, from about 40,000 Da to about 75,000 Da, or from about 50,000 Da to about 75,000 Da.

In a specific embodiment, the PVA can have a MW of from about 13000 Da to about 23000 Da and be 89% hydrolyzed (degree of saponification). In another embodiment, the PVA can have a MW of from about 31,000 Da to about 50,000 Da and be 89% hydrolyzed (degree of saponification).

The amount of PVA in the dissolvable material can vary depending on the desired stiffness and dissolution time. In some embodiments, the PVA can be present in the dissolvable material at about 20 wt. % or more by weight of the dissolvable material, e.g., from about 30 wt. % to about 80 wt. %, from about 40 wt. % to about 70 wt. %, from about 46 wt. % to about 49 wt. %, or from about 90 wt. % to about 97 wt. %. In specific embodiments, the amount of PVA used in the dissolvable material can be 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, or 98 wt. % by weight of the dissolvable material, where any of the stated values can form an upper or lower endpoint of a range. In specific embodiments, the amount of PVA used in the dissolvable material is about 97 wt. % by weight of the material. In other specific embodiments, the amount of PVA used in the dissolvable material is about 91 wt. % by weight of the material. In specific embodiments, the amount of PVA used in the dissolvable material is about 47 wt. % by weight of the material. The weight percentages are based on the total amount of the dissolvable material.

PVP

In specific embodiments, the dissolvable material of the tissue-piercing element can comprise polyvinylpyrrolidone (PVP). PVP is biocompatible and has high strength. In some embodiments, the PVP can have a high K-value, e.g., greater than K-25, greater than K-29, greater than K-32. In a specific embodiment, PVP polymer K90 can be used.

The amount of PVP in the dissolvable material can vary depending on the desired stiffness and dissolution time. In some embodiments, the PVP can be present in the dissolvable material at about 46 wt. % or more by weight of the dissolvable material, e.g., from about 47 wt. % to about 53 wt. %, from about 48 wt. % to about 52 wt. %, or from about 46 wt. % to about 49 wt. %. In specific embodiments, the amount of PVP used in the dissolvable material is about 47 wt. % by weight of the material. The weight percentages are based on the total amount of the dissolvable material.

Protein

In specific embodiments, the dissolvable material of the tissue-piercing element can comprise a protein. In certain examples, the protein can be a gelatin. The gelatin should be biocompatible, have high strength, and high stiffness. In some embodiments, the gelatin can have a Bloom number of from about 0 to about 50, which is sometimes referred to as low Bloom gelatin. In other embodiments, the gelatin can have a Bloom number of from about 51 to about 350. In some embodiments, the gelatin can be gelatin type A or gelatin type B. In some embodiments, the gelatin can be a pork or beef gelatin. In some embodiments, the gelatin can be a fish gelatin, for example, a cold water fish gelatin or warm water fish gelatin.

Further examples of suitable proteins include, but are not limited to, milk protein, whey protein, soy protein, canola protein, including combinations and mixtures thereof.

The MW of the protein can be from about 1,000 Da to about 100,000 Da. For example, the protein can have a MW of from about 1,000 Da to about 75,000 Da, from about 1,000 Da to about 50,000 Da, from about 1,000 Da to about 25,000 Da, from about 10,000 Da to about 100,000 Da, from about 10,000 Da to about 75,000 Da, from about 10,000 Da to about 50,000 Da, from about 25,000 Da to about 100,000 Da, from about 25,000 Da to about 75,000 Da, from about 50,000 Da to about 100,000 Da, or from about 50,000 Da to about 75,000 Da. In a specific embodiment, the protein can have a MW of about 60,000 Da.

In a specific embodiment, gelatin from cold water fish and having a MW of about 60,000 Da can be used.

The amount of protein in the dissolvable material can vary depending on the desired stiffness and dissolution time. In some embodiments, the protein can be present in the dissolvable material at about 46 wt. % or more by weight of the dissolvable material, e.g., from about 47 wt. % to about 53 wt. %, from about 48 wt. % to about 52 wt. %, or from about 46 wt. % to about 49 wt. %. In specific embodiments, the amount of protein used in the dissolvable material is about 47 wt. % by weight of the material. The weight percentages are based on the total amount of the dissolvable material.

Polysaccharide

In specific embodiments, the dissolvable material of the tissue-piercing element can comprise a polysaccharide. The polysaccharide can be used as a binder. Examples of suitable polysaccharides include gum arabic, alginate, chitin, chitosan, carrageenan, pectin, starch, polysorbiton, maltodextrin, dextran, cyclodextrin, polydextrose, cellulose, methyl cellulose, ethyl cellulose, hydropropylmethylcellulose, carboxymethylcellulose (CMC).

The MW of the polysaccharide can be from about 25,000 Da to about 150,000 Da. For example, the polysaccharide can have a MW of from about 25,000 Da to about 125,000 Da, from about 25,000 Da to about 100,000 Da, from about 25,000 Da to about 75,000 Da, from about 50,000 Da to about 150,000 Da, from about 50,000 Da to about 125,000 Da, from about 50,000 Da to about 100,000 Da, from about 75,000 Da to about 150,000 Da, from about 75,000 Da to about 125,000 Da, or from about 75,000 Da to about 100,000 Da. In a specific embodiment, the polysaccharide can a MW of about 90,000 Da.

In a specific embodiment, the polysaccharide can be CMC with a MW of 90,000 Da.

The amount of polysaccharides in the dissolvable material can vary depending on the desired stiffness and dissolution time. In some embodiments, the polysaccharides can be present in the dissolvable material at from about 2 wt. % to about 10 wt. % by weight of the dissolvable material, e.g., from about 3 wt. % to about 4 wt. %, from about 4 wt. % to about 5 wt. %, from about 5 wt. % to about 6 wt. %, from about 6 wt. % to about 7 wt. %, from about 7 wt. % to about 8 wt. %, from about 8 wt. % to about 9 wt. %, from about 9 wt. % to about 10 wt. %, from about 3 wt. % to about 9 wt. %, or from about 6 wt. % to about 9 wt. %. In specific embodiments, the amount of polysaccharides used in the dissolvable material can be about 2, 3, 4, 5, 6, 7, 8, 9, or 10 wt. % by weight of the material, where any of the stated values can form an upper or lower endpoint of a range. The way percentages are based on the total amount of the dissolvable material.

Different combinations of materials can be chosen depending on the particular device and objectives. In general, the dissolvable material can comprise PVA and either PVP or protein, with an optional polysaccharide as a binder. In further examples, the dissolvable material can comprise PVA, PVP, and protein, with an optional polysaccharide as a binder. Specific embodiments include materials comprising about 46-49 wt. % PVA, about 46-49 wt. % gelatin, and about 2-8 wt. % CMC; about 46-49 wt. % PVA, about 46-49 wt. % PVP, and about 2-8 wt. % CMC; about 47 wt. % PVA, about 47 wt. % gelatin, and about 6 wt. % CMC; about 48 wt. % PVA, about 48 wt. % PVP, and about 3-4 wt. % CMC; about 97 wt. % PVA and about 3 wt. % CMC; or about 91 wt. % PVA and about 9 wt. % CMC.

Other examples of water soluble polymers that can be used in the dissolvable material can be chosen from polyaliphatic alcohols such as polyethylene oxide and derivatives thereof including polyethylene glycol (PEG), PEG-acrylates, polyethylene imine, polyvinyl acetate, and derivatives thereof; poly(vinyl)phosphate, poly(vinyl)phosphonic acid, and derivatives thereof; polyacrylic acids and derivatives thereof; polyorganic acids, such as polymaleic acid, and derivatives thereof; polyamino acids, such as polylysine, and polyimino acids, such as polyimino tyrosine, and derivatives thereof; co-polymers and block co-polymers, such as poloxamer 407 or Pluronic L-101™ polymer, and derivatives thereof; tert-polymers and derivatives thereof; polyethers, such as poly(tetramethylene ether glycol), and derivatives thereof; naturally occurring polymers, such as zein and pullulan, and derivatives thereof; polyimide, such as polyntris(hydroxymethyl)methylmethacrylate, and derivatives thereof; surfactants, such as polyoxyethylene sorbitan, and derivatives thereof; polyesters such as poly(ethylene glycol) (n)monomethyl ether mono(succinimidylsuccinate)ester, and derivatives thereof; branched and cyclo-polymers, such as branched PEG and cyclodextrins, and derivatives thereof; and polyaldehydes, such as poly(perfluoropropylene oxide-b-perfluoroformaldehyde), and derivatives thereof.

Dissolvable Sheath

One aspect of the present embodiments includes the realization that the material of analyte sensor membranes is soft, and tends to peel back as the sensor advances into tissue. This problem is especially acute for sensors that are formed by a process in which they are first coated with a membrane and then sharpened at the tip. This process exposes the sensor body, and leaves a thin coating of the membrane surrounding the sides of the sensor body at the tip. Some of the present embodiments provide solutions to this problem.

Figure 4:
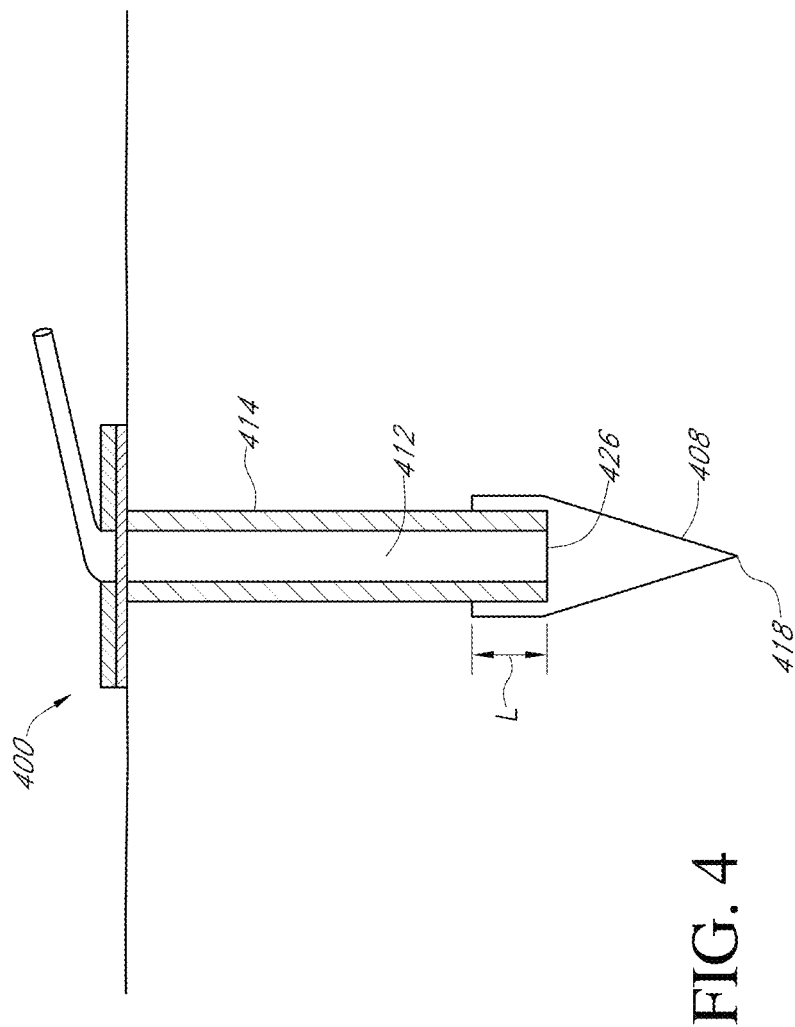
FIG. 4 is a continuous analyte sensor according to the present embodiments.

Referring to FIG. 1, in some embodiments, the tissue-piercing element 108 comprising dissolvable material can comprise a coating that covers at least a portion of the sensor body 112, including the sensor tip 126. For example, with reference to FIG. 4, a length L of the distal end of the sensor body 412 and membrane 414 can be dipped in a liquid bath (not shown) or placed in a mold (also not shown). The length L can be chosen to coat enough of the sensor tip to achieve good adhesion without covering any electrodes on the sensor. For example, L can be in the range of 0.1-4 mm, such as 2-3 mm. As the sensor is withdrawn from the bath or removed from the mold, the sheath remains over the length L, and extends distally from the sensor body tip 426, forming a dissolvable tissue-piercing tip 408. The portion extending from the sensor tip may be sharpened to produce a tissue-piercing coating tip 418.

Figure 5:
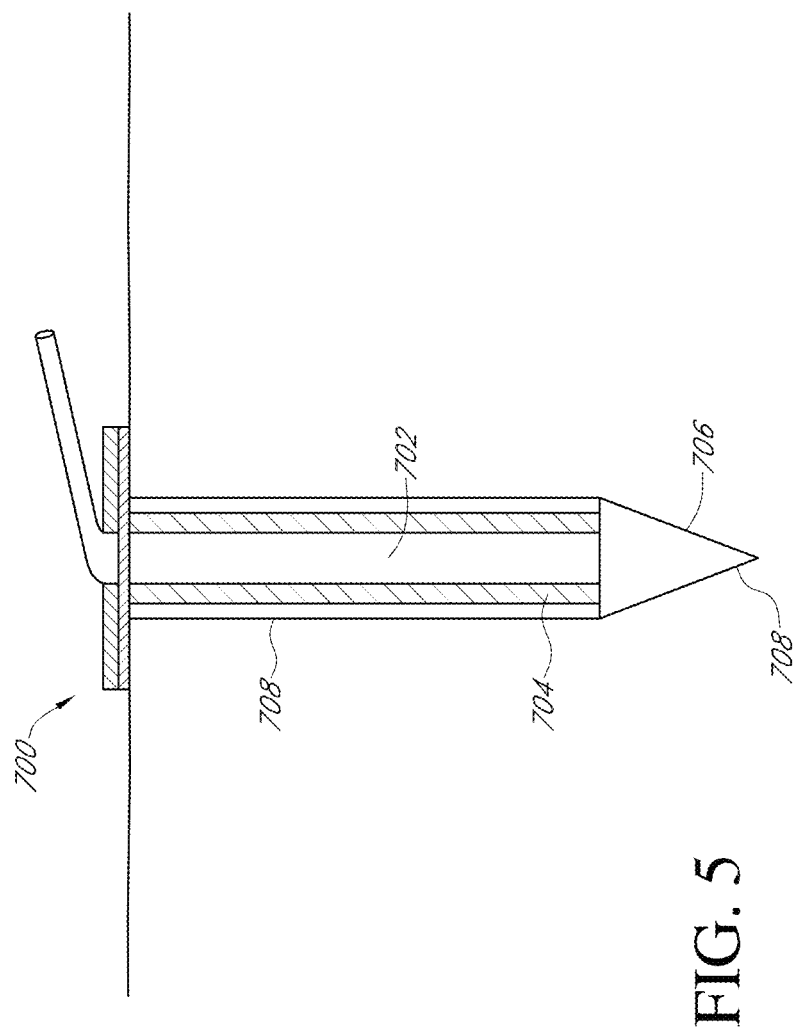
FIG. 5 is a continuous analyte sensor according to the present embodiments.

FIG. 5 illustrates a sensor unit 700 similar to the sensor device 100 described above and shown in FIG. 1. The sensor unit 700 includes a sensor body 702 at least partially covered by a membrane 704. There sensor unit 700 also includes a tissue-piercing element 708 that tapers to a point 706 at the distal end of the tissue piercing element. The sensor unit 700 also include a sheath 708 around the membrane 704 and sensor body 702. The sheath 708 can be made of the same dissolvable material as the tissue piercing element 708.

Figure 6:
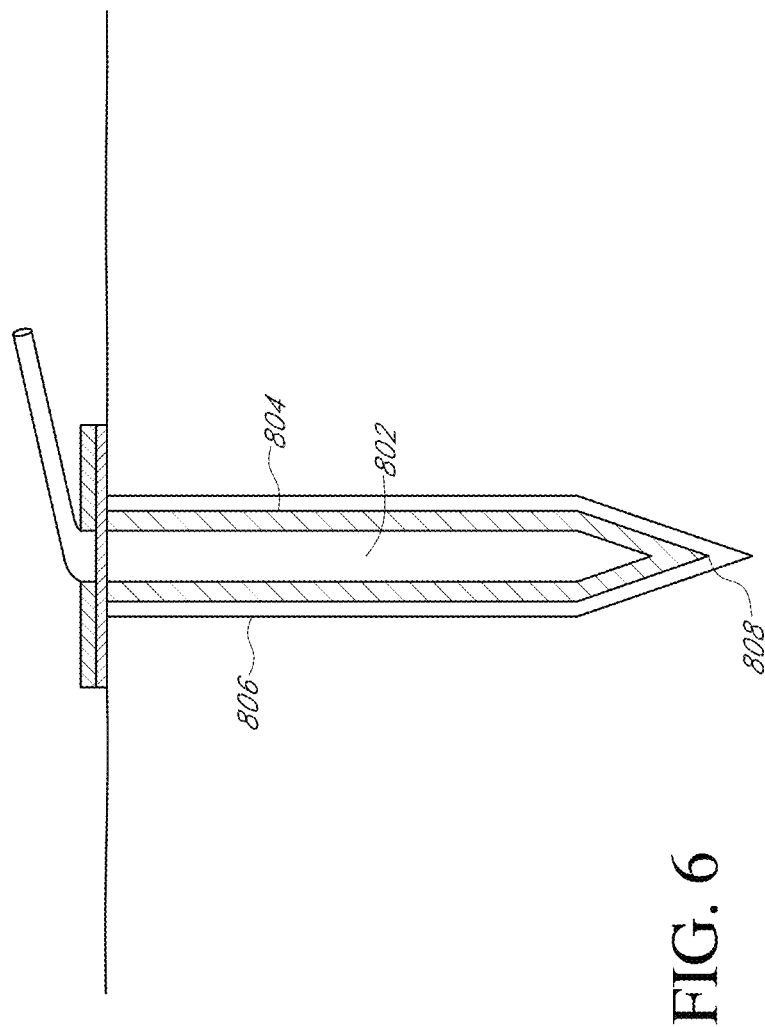
FIG. 6 is a continuous analyte sensor according to the present embodiments.

In an alternative embodiment illustrated in FIG. 6, the sensor body 802 may be sharpened prior to being coated with the membrane 804, so that the sharpened tip 808 is covered with membrane 804. The membrane 804 can then be coated with a sheath 806. The sheath 806 can cover the tip 808 of the membrane 804.

The sheath can be made of the same dissolvable material used to make the tissue-piercing element. Alternatively, the sheath can be made of a different, dissolvable material. In such embodiments, the dissolvable tip can be such that it dissolves before the dissolvable sheath, or the dissolvable tip can be such that it dissolves after the dissolvable sheath. As noted above, the dissolvable material for the sheath should dissolve, not degrade, and leave the membrane unchanged from its pre-coated state.

As a result of the sheath, the sensor device can have a buckling strength sufficient to penetrate the host's skin without the need for a guiding needle. For example, the coated sensor devices disclosed herein can have a buckling strength of at least about 0.040 lbf, e.g., at least about 0.050 lbf, 0.10 lbf, 0.15 lbf, or 0.20 lbf, where any of the stated values can form an upper or lower endpoint of a range. The buckling strength can be less than 1.0 lbf. Buckling strength is measured on a sample from about 100 µm to about 500 µm in diameter.

As discussed above, the sensor 400 may include one or more aspects that either suppress wounding, or promote rapid healing, or both. In certain embodiments, these aspects may be present in the dissolvable tip 408 or sheath. For example, one or more bioactive agents may be integrated into the dissolvable tip 408 or sheath by combining it with the material of the liquid bath during the dipping or molding process. Alternatively, the dissolvable tip 408 or sheath may be dipped in a subsequent liquid bath that coats the dissolvable tip 408 with one or more bioactive agents. Alternatively, the dissolvable tip 408 or sheath may be placed in a mold and filled with a liquid that coats the dissolvable tip 408 with one or more bioactive agents. Exemplary bioactive agents are discussed at length above and will not be repeated here. However, certain bioactive agents may, for example, induce osmotic pressure or oncotic pressure.

In some embodiments, one or more layers of one or more polymers and/or bioactive agents may be coated onto the tissue-piercing element. The use of bioactive agents to coat the surface of the tissue-piercing element may provide a release of bioactive agents in the subcutaneous tissue during and/or after insertion of the in vivo portion of the sensor device. In further embodiments, one or more polymer layers may be used to control the release rate of the one or more bioactive agents. Such polymers may include, but are not limited to, parylene, parylene C, parylene N, parylene F, poly(hydroxymethyl-p-xylylene-co-p-xylylene) (PHPX), poly(lactic-co-glycolic acid) (PLGA), polyethylene-co-vinyl acetate (PEVA), Poly-L-lactic acid (PLLA), poly N-butyl methacrylate (PBMA), polypeptide, polyoxazoline (PDX), phosphorylcholine, poly(isobutylene-co-styrene), polyglycolide (PGA), poly(amic acid) (PAA), polyethylene glycol (PEG), derivatives of one or more of these polymers, and combinations or mixtures thereof.

In some embodiments, one or more regions of the surface of the tissue-piercing element may comprise one or more recessed portions (e.g., cavities, indentations, openings, grooves, channels, etc.) configured to serve as reservoirs or depots for holding bioactive agents. The recessed portions may be formed at any preselected location and have any preselected depth, size, geometrical configuration, and dimensions, in accordance with the intended application. Use of reservoirs or depots may increase the amount of bioactive agents the tissue-piercing element is capable of carrying and delivering. In further embodiments, the tissue-piercing element may be hollow with a cavity and connected via various passages with one or more openings on its surface, so that bioactive agents may be released from the cavity via the openings. In some embodiments, for example as shown FIGS. 3A and 3B, the tissue-piercing element 310 comprises a pocket 312 shaped and dimensioned to support a sensor 314 with a membrane disposed thereon.

In certain embodiments, the in vivo portion of the sensor device is configured to remain substantially stationary within the tissue of the host, so that migration or motion of the sensor body with respect to the surrounding tissue is inhibited. Migration or motion may cause inflammation at the sensor implant site due to irritation, and may also cause noise on the sensor signal due to motion-related artifacts. Therefore, it may be advantageous to provide an anchoring mechanism that provides support for the in vivo portion of the sensor device to avoid the aforementioned problems. In some embodiments, the tissue-piercing element may comprise a surface with one or more regions that are textured.

Texturing may roughen the surface of the tissue-piercing element and thereby provide a surface contour with a greater surface area than that of a non-textured (e.g., smooth) surface. Accordingly, the amount of bioactive agents, polymers, and/or coatings that the tissue-piercing element may carry and be released in situ is increased, as compared to that with a non-textured surface. Furthermore, it is believed that a textured surface may also be advantageous in some instances, because the increased surface area may enhance immobilization of the in vivo portion of the sensor device within the tissue of the host. In certain embodiments, the tissue-piercing element may comprise a surface topography with a porous surface (e.g. porous parylene), ridged surface, etc. In certain embodiments, the anchoring may be provided by prongs, spines, barbs, wings, hooks, a bulbous portion (for example, at the distal end), an S-bend along the tissue-piercing element, a gradually changing diameter, combinations thereof, etc., which may be used alone or in combination to stabilize the sensor within the subcutaneous tissue. For example, in certain embodiments, the tissue-piercing element may comprise one or more anchoring members configured to splay outwardly (e.g., in a direction toward a plane perpendicular to the longitudinal axis of the sensor unit) during or after insertion of the sensor unit. Outward deployment of the anchoring member facilitates anchoring of the sensor unit, as it results in the tissue-piercing element pressing against the surrounding tissue, and thus reduces (or prevents) movement and/or rotation of the sensor unit. In some embodiments, the anchoring members are formed of a shape memory material, such as nitinol, which may be configured to transform from a martensitic state to an austenitic state at a specific temperature (e.g., room temperature or body temperature). In the martensitic state, the anchoring members are ductile and in a contracted configuration. In the austenitic state, the anchoring members deploy to form a larger predetermined shape while becoming more rigid. While nitinol is described herein as an example of a shape memory material that may be chosen to form the anchoring member, it should be understood that other similar materials (e.g., shape memory material) may also be used.

The tissue-piercing element of the sensor device may be introduced subcutaneously at any of a variety of angles with respect to the mounting surface (the bottom surface of the mounting unit), and thus the skin surface. For example, in some embodiments the distal tip of the tissue-piercing element may extend substantially perpendicular to the mounting surface, but in other embodiments, the distal tip may extend at an angle with respect to the mounting surface of about 15°, 20°, 30°, 40°, 45°, 60°, 75°, 80°, 90°, 105°, 100°, 120°, 135°, 140°, 150°, 160°, or 165°, for example.

As illustrated in FIG. 1, the sensor device 100 may include a skin-contacting mounting unit 116 configured to be secured to a host. In some embodiments, the mounting unit 116 comprises a base 122 adapted for fastening to a host's skin. The base 122 may be formed from a variety of hard or soft materials and may comprise a low profile for reducing protrusion of the sensor device from the host during use. In some embodiments, the base 122 is formed at least partially from a flexible material configured to conform to skin contour, so as to reduce or eliminate motion-related artifacts associated with movement by the host. In certain embodiments, the base 122 of the mounting unit 116 includes an adhesive material or adhesive layer 124, also referred to as an adhesive pad, preferably disposed on the mounting unit's bottom surface, and may include a releasable backing layer (not shown). Thus, removing the backing layer and pressing the base 122 of the mounting unit 116 onto the host's skin 104 adheres the mounting unit 116 to the host's skin 104. Appropriate adhesive layers may be chosen and designed to stretch, elongate, conform to, and/or aerate the region (e.g. host's skin). In some embodiments, the mounting unit comprises a guiding portion (not shown) configured to guide insertion of the sensor device 100 through the host's skin 104 and to support a column strength of the support member 112 such that the sensor device 100 is capable of being inserted through the host's skin 104 without substantial buckling.

Figure 3A:
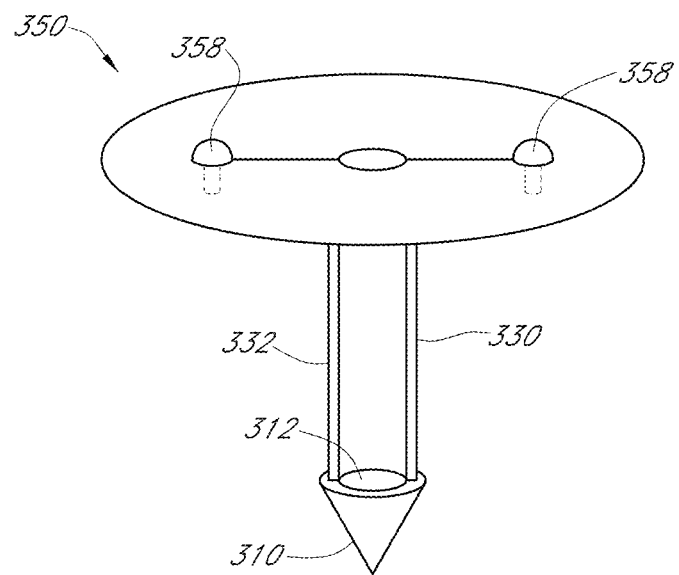
FIGS. 3A-3D are top perspective views of additional continuous analyte sensors according to the present embodiments.
Figure 3B:
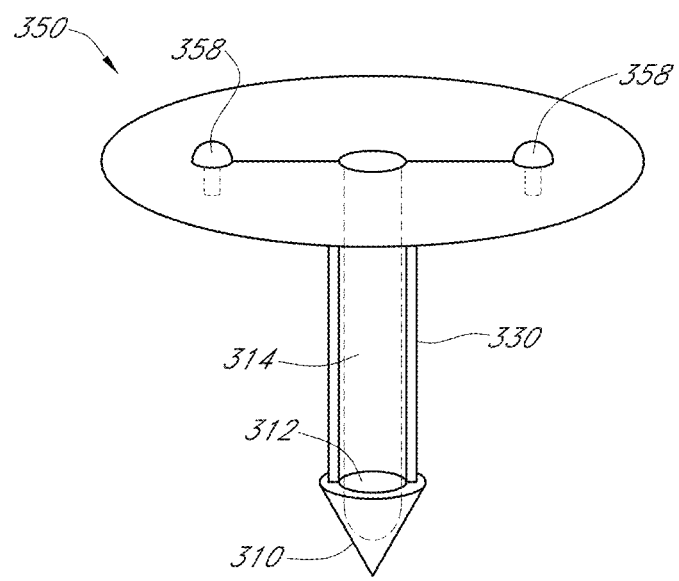
Figure 3C:
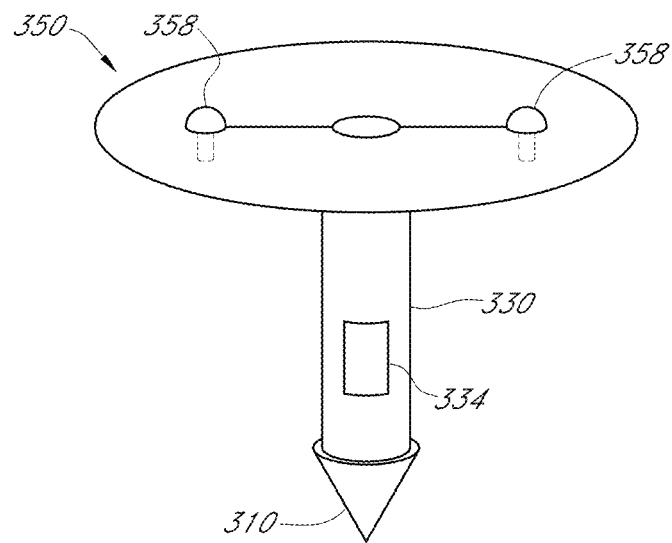
Figure 3D:
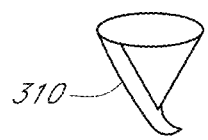

While FIG. 1 illustrates one configuration for providing membrane protection, other sensor body configurations may also be used. For example, some of the sensor bodies described herein may include a support member 330 configured to partially surround a sensor, as illustrated in FIGS. 3A and 3B, or configured to substantially surround a sensor, as illustrated in FIG. 3C. Unlike other embodiments described elsewhere herein, in the embodiments illustrated in FIGS. 3A-3C, the support member 330 does not comprise a working electrode. Rather, one or more working electrodes are arranged as components distinct from the support member 330. In some embodiments, the support member 330 may also serve as a reference electrode.

In the embodiment illustrated in FIG. 3A, the support member 330 comprises a longitudinal recess 332 configured to at least partially accommodate a sensor (e.g., a working electrode with a membrane disposed thereon). In some embodiments, the longitudinal recess may have a length corresponding to less than about 90% of the length of the support member 330, or less than about 75%, or less than about 50%, or less than about 33%, or less than about 25%. In other embodiments, the longitudinal recess may extend substantially across the entire length of the support member 330, as illustrated in FIG. 3B. In certain embodiments, the support member 330 may surround more than about 10% of the outer perimeter (e.g., circumference) of the sensor, or more than about 25%, or more than about 33%, or more than about 50%, or more than about 75%.

As illustrated in FIG. 3C, in some embodiments wherein the sensor (e.g., the working electrode) is substantially surrounded by the support member 330. The support member 330 may be provided with one or more window portions 334 (openings or slots extending through the wall thickness of the support member 330) that expose certain portions of the electrode to biological fluid (e.g., interstitial fluid), and thus allow biological fluid to diffuse toward and contact the working electrode's electroactive surface and the membrane disposed thereon. In this embodiment, the working electrode and the membrane disposed thereon are essentially housed within the support member 330, and are thus protected during packing, handling, and/or insertion of the device. The window portions 334 may have any of a variety of shapes and dimensions. For example, in some embodiments, the window portions may be formed to have a circular or substantially circular shape, but in other embodiments, the electrode may be formed with a shape resembling an ellipse, a polygon (e.g., triangle, square, rectangle, parallelogram, trapezoid, pentagon, hexagon, octagon), or the like. In certain embodiments, the window portions may comprise sections that extend around the perimeter of the longitudinal cross section of the support member. For example, the support member may be made by using a hypo-tube with window portions cut out in a spiral configuration, by ablation, etching, or other techniques.

Protective Covering

Sometimes during sensor manufacturing, there are several processes that can damage the sensor including general handling of the sensor, loading into cannula/needle assemblies, corrosion, and other types of mechanical/chemical changes to membrane that may be not desired.

With a dissolvable material coating, as disclosed herein, the dissolvable material can protect the sensors from such damage. For example, the resistance layer (RL) can be protected from damage during sensor handling and loading processes. With the correct selection of dissolvable material, it can also prevent the reference region of the sensor from contacting the stainless steel needle, which can cause corrosion when exposed to high temperature, humidity, etc. Furthermore, any contaminents from sensor loading/deployment will not be physically touching, adsorbed, absorbed, or coated onto the RL membrane. This feature can be especially important when there will be specialized coatings outside the RL that will not function properly unless they are "clean" and without damage.

Disclosed herein are sensor devices that comprise a protective covering around a sensor membrane where the protective covering comprises a dissolvable material as disclosed herein.

Permeability

Conventional glucose sensors measure current in the nanoAmp range. In contrast to conventional glucose sensors, the preferred embodiments are configured to measure the current flow in the picoAmp range, and in some embodiments, femtoAmps. Namely, for every unit (mg/dL) of glucose measured, at least one picoAmp of current is measured. In some embodiments, from about 1, 2, 3, 4, or 5 picoAmps to about 25, 50, 100, 250, or 500 picoAmps of current is measured for every unit (mg/dl) of glucose measured.

Bioactive Agents

A variety of bioactive agents are known to promote fluid influx or efflux. Accordingly, incorporation of bioactive agents into the membrane may increase fluid bulk, bulk fluid flow, and/or diffusion rates (and promoting glucose and oxygen influx), thereby decrease non-constant noise. In some embodiments, fluid bulk and/or bulk fluid flow are increased at (e.g., adjacent to the sensor exterior surface) the sensor by incorporation of one or more bioactive agents. In some embodiments, the sensor is configured to include a bioactive agent that irritates the wound and stimulates the release of soluble mediators that are known to cause a local fluid influx at the wound site. In some embodiments, the sensor is configured to include a vasodilating bioactive agent, which may cause a local influx of fluid from the vasculature.

A variety of bioactive agents may be found useful in preferred embodiments. Example bioactive agents include but are not limited to blood-brain barrier disruptive agents and vasodilating agents, vasodilating agents, angiogenic factors, and the like. Useful bioactive agents include but are not limited to mannitol, sodium thiosulfate, VEGF/VPF, NO, NO-donors, leptin, bradykinin, histamines, blood components, platelet rich plasma (PRP), matrix metalloproteinases (MMP), Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-1 (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Leptin, Copper Sulphate, Estradiol, prostaglandins, cox inhibitors, endothelial cell binding agents (for example, decorin or vimentin), glenipin, hydrogen peroxide, nicotine, and Growth Hormone. Still other useful bioactive agents include enzymes, cytotoxic or necrosing agents (e.g., pactataxyl, actinomycin, doxorubicin, daunorubicin, epirubicin, bleomycin, plicamycin, mitomycin), cyclophosphamide, chlorambucil, uramustine, melphalan, bryostatins, inflammatory bacterial cell wall components, histamines, pro-inflammatory factors and the like.

Bioactive agents may be added during manufacture of the sensor by incorporating the desired bioactive agent in the manufacturing material for one or more sensor layers or into an exterior biomaterial, such as a porous silicone membrane. For example, bioactive agents may be mixed with a solution during membrane formation, which is subsequently applied onto the sensor during manufacture. Alternatively, the completed sensor may be dipped into or sprayed with a solution of a bioactive agent, for example. The amount of bioactive agent may be controlled by varying its concentration, varying the indwell time during dipping, applying multiple layers until a desired thickness is reached, and the like, as disclosed elsewhere herein. In an alternative embodiment, the bioactive agent is microencapsulated before application to the sensor. For example, microencapsulated bioactive agent may be sprayed onto a completed sensor or incorporated into a structure, such as an outer mesh layer or a shedding layer. Microencapsulation may offer increased flexibility in controlling bioactive agent release rate, time of release occurrence and/or release duration.

In some embodiments chemical systems/methods of irritation may be incorporated into an exterior sensor structure, such as the biointerface membrane (described elsewhere herein) or a shedding layer that releases the irritating agent into the local environment. For example, in some embodiments, a "shedding layer" releases (e.g., sheds or leaches) molecules into the local vicinity of the sensor and may speed up osmotic fluid shifts. In some embodiments, a shedding layer may provide a mild irritation and encourage a mild inflammatory/foreign body response, thereby preventing cells from stabilizing and building up an ordered, fibrous capsule and promoting fluid pocket formation.

A shedding layer may be constructed of any convenient, biocompatible material, include but not limited to hydrophilic, degradable materials such as polyvinylalcohol (PVA), PGC, Polyethylene oxide (PEO), polyethylene glycol-polyvinylpyrrolidone (PEG-PVP) blends, PEG-sucrose blends, hydrogels such as polyhydroxyethyl methacrylate (pHEMA), polymethyl methacrylate (PMMA) or other polymers with quickly degrading ester linkages. In certain embodiment, absorbable suture materials, which degrade to compounds with acid residues, may be used. The acid residues are chemical irritants that stimulate inflammation and wound healing. In certain embodiments, these compounds include glycolic acid and lactic acid based polymers, polyglactin, polydioxone, polydyconate, poly(dioxanone), poly(trimethylene carbonate) copolymers, and poly(caprolactone) homopolymers and copolymers, and the like.

In other example embodiments, the shedding layer may be a layer of materials listed elsewhere herein for the first domain, including copolymers or blends with hydrophilic polymers such as polyvinylpyrrolidone (PVP), polyhydroxyethyl methacrylate, polyvinylalcohol, polyacrylic acid, polyethers, such as polyethylene glycol, and block copolymers thereof including, for example, di-block, tri-block, alternating, random and graft copolymers (block copolymers are discussed in U.S. Pat. No. 4,803,243 and U.S. patent). In one preferred embodiment, the shedding layer is comprised of polyurethane and a hydrophilic polymer. For example, the hydrophilic polymer may be polyvinylpyrrolidone. In one preferred embodiment, the shedding layer is polyurethane comprising not less than 5 weight percent polyvinylpyrrolidone and not more than 45 weight percent polyvinylpyrrolidone. Preferably, the shedding layer comprises not less than 20 weight percent polyvinylpyrrolidone and not more than 35 weight percent polyvinylpyrrolidone and, most preferably, polyurethane comprising about 27 weight percent polyvinylpyrrolidone.

In other example embodiments, the shedding layer may include a silicone elastomer, such as a silicone elastomer and a poly(ethylene oxide) and poly(propylene oxide) co-polymer blend, as disclosed in copending U.S. patent application Ser. No. 11/404,417 filed Apr. 14, 2006. In one embodiment, the silicone elastomer is a dimethyl- and methylhydrogen-siloxane copolymer. In one embodiment, the silicone elastomer comprises vinyl substituents. In one embodiment, the silicone elastomer is an elastomer produced by curing a MED-4840 mixture. In one embodiment, the copolymer comprises hydroxy substituents. In one embodiment, the co-polymer is a triblock poly(ethylene oxide)-poly(propylene oxide)-poly(ethylene oxide) polymer. In one embodiment, the co-polymer is a triblock poly(propylene oxide)-poly(ethylene oxide)-poly(propylene oxide) polymer. In one embodiment, the co-polymer is a PLURONIC® polymer. In one embodiment, the co-polymer is PLURONIC® F-127. In one embodiment, at least a portion of the co-polymer is cross-linked. In one embodiment, from about 5% w/w to about 30% w/w of the membrane is the co-polymer.

A shedding layer may take any shape or geometry, symmetrical or asymmetrical, to promote fluid influx in a desired location of the sensor, such as the sensor head or the electrochemically reactive surfaces, for example. Shedding layers may be located on one side of sensor or both sides. In another example, the shedding layer may be applied to only a small portion of the sensor or the entire sensor.

In one example embodiment, a shedding layer comprising polyethylene oxide (PEO) is applied to the exterior of the sensor, where the tissue surrounding the sensor may directly access the shedding layer. PEO leaches out of the shedding layer and is ingested by local cells that release pro-inflammatory factors. The pro-inflammatory factors diffuse through the surrounding tissue and stimulate an inflammation response that includes an influx of fluid. Accordingly, early noise may be reduced or eliminated and sensor function may be improved.

In another example embodiment, the shedding layer is applied to the sensor in combination with an outer porous layer, such as a mesh or a porous biointerface as disclosed elsewhere herein. In one embodiment, local cells access the shedding layer through the through pores of a porous silicone biointerface. In one example, the shedding layer material is applied to the sensor prior to application of the porous silicone. In another example, the shedding layer material may be absorbed into the lower portion of the porous silicone (e.g., the portion of the porous silicone that will be proximal to the sensor after the porous silicone has been applied to the sensor) prior to application of the porous silicone to the sensor.

Wound Suppression

Non-constant noise may be decreased by wound suppression (e.g., during sensor insertion), in some embodiments. Wound suppression includes any systems or methods by which an amount of wounding that occurs upon sensor insertion is reduced and/or eliminated. While not wishing to be bound by theory, it is believed that if wounding is suppressed or at least significantly reduced, the sensor will be surrounded by substantially normal tissue (e.g., tissue that is substantially similar to the tissue prior to sensor insertion). Substantially normal tissue is believed to have a lower metabolism than wounded tissue, producing fewer interferents and reducing early noise.

Wounds may be suppressed by adaptation of the sensor's architecture to one that either suppresses wounding or promotes rapid healing, such as an architecture that does not cause substantial wounding (e.g., an architecture configured to prevent wounding), an architecture that promotes wound healing, an anti-inflammatory architecture, etc. In one example embodiment, the sensor is configured to have a low profile, a zero-footprint or a smooth surface. For example, the sensor may be formed of substantially thin wires, such as wires from about 50 μm to about 116 μm in diameter, for example. Preferably, the sensor is small enough to fit within a very small gauge needle, such as a 30, 31, 32, 33, 34, or 35 gauge needle (or smaller) on the Stubs scale, for example. In general, a smaller needle, the more reduces the amount of wounding during insertion. For example, a very small needle may reduce the amount of tissue disruption and thereby reduce the subsequent wound healing response. In an alternative embodiment, the sensor's surface is smoothed with a lubricious coating, to reduce wounding upon sensor insertion.

Wounding may also be reduced by inclusion of wound-suppressive agents (bioactive agents) that either reduce the amount of initial wounding or suppress the wound healing process. While not wishing to be bound by theory, it is believed that application of a wound-suppressing agent, such as an anti-inflammatory, an immunosuppressive agent, an anti-infective agent, or a scavenging agent, to the sensor may create a locally quiescent environment and suppress wound healing. In a quiescent environment, bodily processes, such as the increased cellular metabolism associated with wound healing, may minimally affect the sensor. If the tissue surrounding the sensor is undisturbed, it may continue its normal metabolism and promote sensor function.

In some embodiment, useful compounds and/or factors for suppressing wounding include but are not limited to first-generation H1-receptor antagonists: ethylenediamines (e.g., mepyramine (pyrilamine), antazoline), ethanolamines (e.g., diphenhydramine, carbinoxamine, doxylamine, clemastine, and dimenhydrinate), alkylamines (pheniramine, chlorphenamine (chlorpheniramine), dexchlorphenamine, brompheniramine, and triprolidine), piperazines (cyclizine, hydroxyzine, and meclizine), and tricyclics (promethazine, alimemazine (trimeprazine), cyproheptadine, and azatadine); second-generation H1-receptor antagonists such as acrivastine, astemizole, cetirizine, loratadine, mizolastine, azelastine, levocabastine, and olopatadine; mast cell stabilizers such as cromoglicate (cromolyn) and nedocromil; anti-inflammatory agents, such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (e.g., L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; corticosteroids such as cortisone, hydrocortisone, methylprednisolone, prednisone, prednisolone, betamethasone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone; immunosuppressive and/or immunomodulatory agents such as anti-proliferative, cell-cycle inhibitors (e.g., paclitaxel, cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivastatin), E. coli heat-labile enterotoxin, and advanced coatings; anti-infective agents, such as anthelmintics (mebendazole); antibiotics such as aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim; interferent scavengers, such as superoxide dismutase (SOD), thioredoxin, glutathione peroxidase and catalase, anti-oxidants, such as uric acid and vitamin C, iron compounds, Heme compounds, and some heavy metals; artificial protective coating components, such as albumin, fibrin, collagen, endothelial cells, wound closure chemicals, blood products, platelet-rich plasma, growth factors and the like.

While not wishing to be bound by theory, it is believed that, in addition to the analyte sensor configurations described elsewhere herein, application of a lubricious coating to the sensor may substantially reduce and/or suppress noise occurrence by substantially preventing injury to the host. Accordingly, in some embodiments, a lubricious coating may be applied to the in vivo portion of the sensor to reduce the foreign body response to the implanted sensor. The term "lubricous coating" as used herein is used in its ordinary sense, including without limitation, a surface treatment that provides a reduced surface friction. A variety of polymers are suitable for use as a lubricious sensor coating, such as but not limited to Teflon, polyethylene, polycarbonate, polyurethane, poly(ethylene oxide), poly(ethylene oxide)-poly(propylene oxide) copolymers, and the like. In one example embodiment, one or more layers of HydroMed™, a polyether-polyurethane manufactured by CardioTech International, Inc. (Wilmington, Mass.) is applied to the sensor (e.g., over the resistance domain).

Methods of Making

In one embodiment, a method of making a sensor device comprises coating a wire with a membrane. The coated wire is then cut to a desired length to form a sensor wire having a tip. Example methods for performing these steps are described in U.S. Patent Application Publication No. 2011/0027453, the entire contents of which are hereby incorporated by reference herein. The coated sensor wire is then coated with a dissolvable material as disclosed herein.

Exposing the coated sensor wire to the dissolvable material may comprise dipping at least the sensor tip in a liquid bath of the dissolvable material. After the sensor wire is withdrawn from the liquid bath, the membrane is cured to harden the dissolvable material. Thereafter, the sensor wire may be sharpened prior to applying the membrane to the sensor wire, or after applying the membrane to the sensor wire but prior to applying the dissolvable material.

In any of the foregoing embodiments, the wire may be a shape memory metal (or a more rigid metal like Ti). In such embodiments, the wire may be held in a first position, which may be curved or straight, and during the insertion process the wire returns to its memorized shape, which may be curved or straight. The return to the memorized shape may release stored spring energy in the wire, creating a whipping action that facilitates piercing the skin.

In another embodiment, a method of making a sensor device comprises coating a wire with a membrane. The coated wire is then inserted into a mold, which is then filled with a liquid bath of the dissolvable material. After a period of time sufficient to form the tissue piercing element, the mold is removed or the coated wire is removed from the mold.

In another embodiment, a method of making a sensor device comprises dipping at least a tip of a sensor into a liquid bath of the dissolvable material to form a coating of the liquid on the sensor tip; and withdrawing the sensor tip from the liquid while controlling parameters of the withdrawal so that the coating forms a tissue-piercing element extending from the sensor tip, wherein the coating comprises a dissolvable material that dissolves upon insertion into the host.

In another embodiment, a method of making a sensor device comprises inserting at least a tip of a sensor into a mold; adding a liquid bath of the dissolvable material to the mold; and separating the sensor from the mold when the liquid has dried and formed a tissue-piercing element extending from the sensor tip, wherein the coating comprises a dissolvable material that dissolves upon insertion into the host.

In these methods, the liquid bath of the dissolvable material can be prepared by making an aqueous solution or mixture of the polymers disclosed herein (e.g., PVA, PVP, protein and/or polysaccharide) in an amount such that after drying the liquid the remaining dissolvable material has the desired amount of the polymers. For example, PVA can be added to the liquid bath at from about 1 wt. % to about 70 wt. % by weight of the liquid bath, e.g., from about 5 wt. % to about 50 wt. %, from about 10 wt. % to about 40 wt. %, from about 15 wt. % to about 30 wt. %. In specific embodiments, the amount of PVA used in the bath can be about 30 wt. % by weight of the liquid bath. In specific embodiments, the amount of PVA used can be about 15 wt. % by weight of the liquid bath. The weight percentages are based on the total amount of the liquid bath.

Likewise, the amount of PVP can be from about 1 wt. % to about 45 wt. % by weight of the liquid bath, e.g., from about 5 wt. % to about 35 wt. %, from about 10 wt. % to about 30 wt. %, from about 15 wt. % to about 25 wt. %. In specific embodiments, the amount of PVP used in the liquid bath can be about 15 wt. % by weight of the liquid bath. The weight percentages are based on the total amount of the liquid bath.

The amount of proteins can at from about 1 wt. % to about 45 wt. % by weight of the liquid bath, e.g., from about 5 wt. % to about 35 wt. %, from about 10 wt. % to about 30 wt. %, from about 15 wt. % to about 25 wt. %. In specific embodiments, the amount of protein used in the liquid bath can be about 15 wt. % by weight of the liquid bath. The way percentages are based on the total amount of the liquid bath with the remainder being water.

The amount of polysaccharides added to the liquid bath can be from about 0.1 wt. % to about 5 wt. % by weight of the liquid bath, e.g., from about 0.5 wt. % to about 3.5 wt. %, or from about 1 wt. % to about 2 wt. %. In specific embodiments, the amount of polysaccharide used in the liquid bath is about 1 or 2 wt. % by weight of the liquid bath.

Different combinations of materials can be chosen depending on the particular device and objectives. In general, the dissolvable material can comprise PVA and either PVP or protein, with an optional polysaccharide as a binder. In further examples, the dissolvable material can comprise PVA, PVP, and protein, with an optional polysaccharide as a binder. Specific embodiments include preparing a liquid bath of dissolvable materials that comprises 15 wt. % PVA, 15 wt. % gelatin, and 2 wt. % CMC; 15 wt. % PVA, 15 wt. % PVP, and 1 wt. % CMC; 30 wt. % PVA and 1 wt. % CMC; or 30 wt. % PVA and 3 wt. % CMC based on the weight of the liquid bath. The balance of these percentages can be water. These polymer combinations can be prepared by dissolving the polymers in water, with optional heating to facilitate dissolution.

EXAMPLES

The following examples are set forth below to illustrate the methods, compositions, devices, and results according to the disclosed subject matter. These examples are not intended to be inclusive of all aspects of the subject matter disclosed herein, but rather to illustrate representative methods, compositions, devices, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Dissolvable Material Formulations

The dissolvable materials used in the following examples were poly(vinyl alcohol-co-cinyl acetate) (PVA), polyvinylpyrrolidone (PVP), gelatin, and carboxy-methyl cellulose (CMC). The PVA had a MW from 13000 Da to 23000 Da, 89% hydrolyzed or a MW from 31,000 Da to 50,000 Da, 89% hydrolyzed. PVA is a biocompatible, inert polymer with beneficial lubricating and binding properties. It has high strength and strong adhesion to the wire. The PVP polymer K90 was used as it is also biocompatible, has high strength, and is compatible with existing membrane coatings. Gelatin from cold water fish skin with a MW of 60,000 Da was used as it is biocompatible, has high strength, and high stiffness. CMC with a MW of 90,000 Da was used as a binding agent.

These materials were chosen because of their biocompatibility, strength, stiffness and binding characteristics. Moreover, since no single material can confer all the required properties to the tip, it is helpful to use a combination of these materials in the final formulation to make the tip/sheath. To identify exemplary formulations, the strength and stiffness of the different combinations was examined. These materials are hygroscopic and take up moisture in humid conditions. Having taken up water, they tend to go soft and lose their strength and stiffness. Hence, the effect of humidity on the strength and Young's Modulus of these materials was also studied.

Films were drawn from the different formulations. Once dry they were cut into dog-bone shapes. Tensile testing was done by fixing both ends of the dog-bones and pulling them apart using a load cell. The films were subjected to 3 conditions: i) Storage with a desiccator overnight (0% humidity), ii) ambient conditions, and iii) storage at 84% humidity overnight (fully saturated polymer film).

Figure 7:
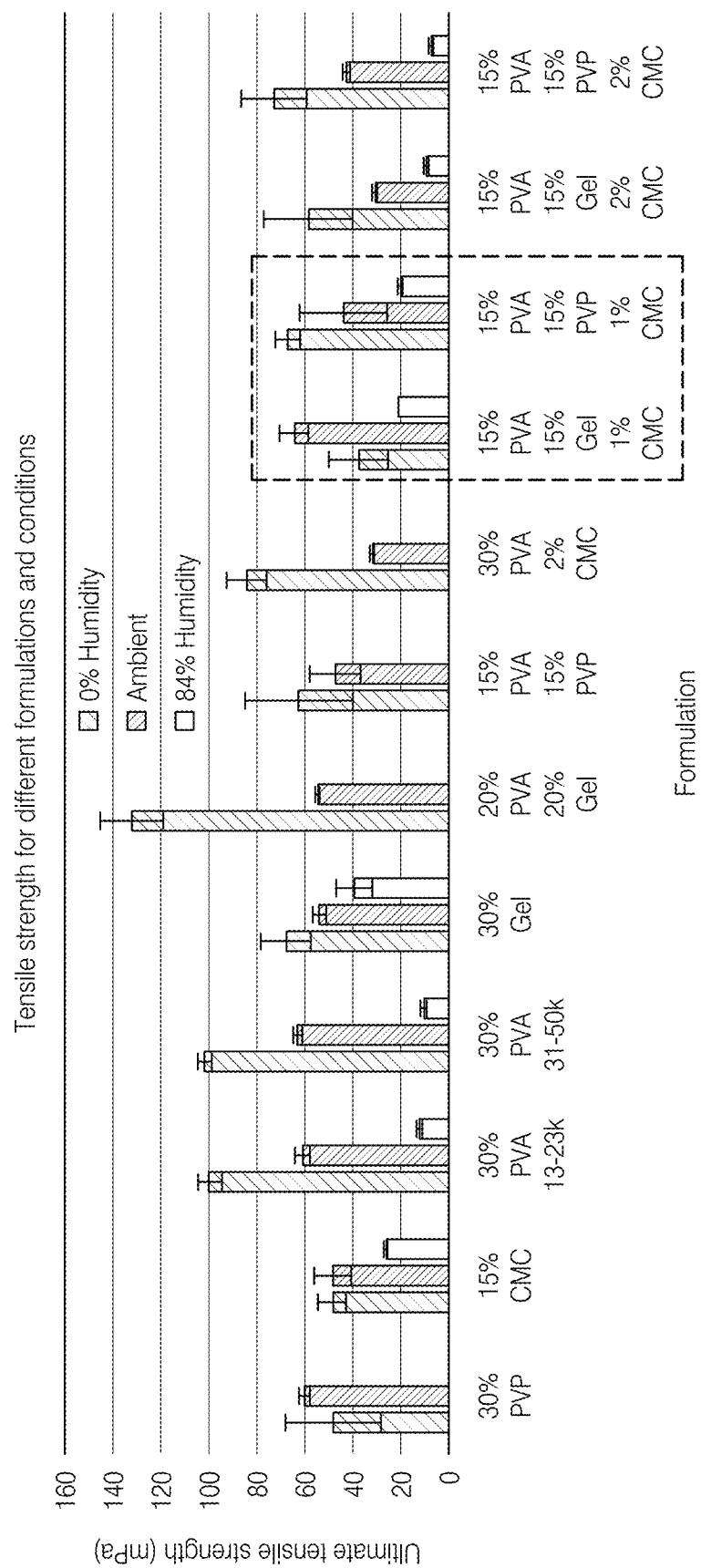
FIG. 7 is a graph of tensile strength of various for different formulations and conditions of tip/sheath coatings.
Figure 8:
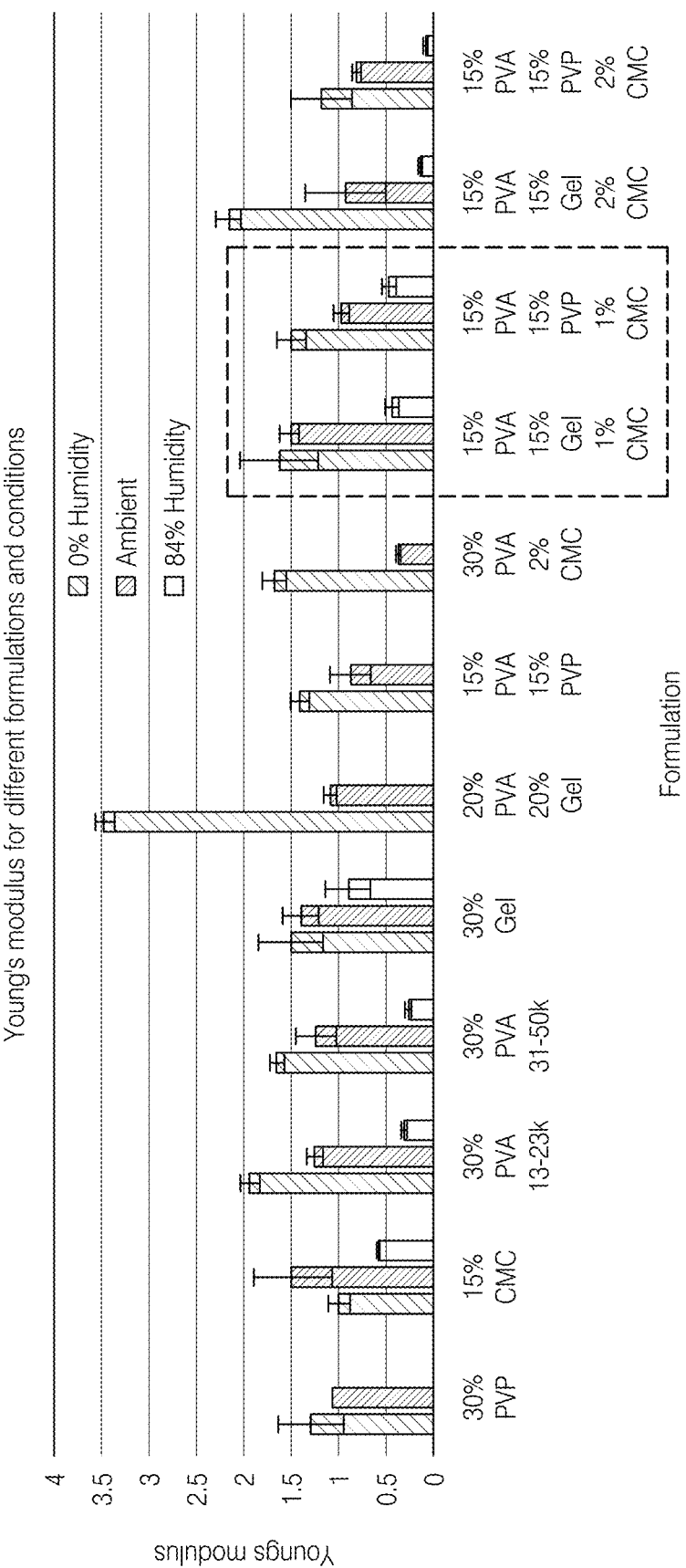
FIG. 8 is a graph of Young's modulus for different formulations and conditions of tip/sheath coatings.

As illustrated in FIGS. 7 and 8, the results show that tensile strength and stiffness of PVA and PVP vary widely with humidity. On the other hand Gel and CMC are less resistant to humidity. A combination of these materials is one way to reduce the effect of humidity on the material properties. Based on these results 15% PVA, 15% Gel, and 1% CMC and 15% PVA, 15% PVP and 1% CMC were chosen as formulations for the following examples. It should be understood that different molecular weights and combinations of these core materials can be used to make the final formulation for the tip/sheath for a particular application. While these variations can be made, the final product should have a tensile strength under various conditions and combinations to be in the range of from about 20 to about 90 MPa, Young's Modulus in the range of from about 1 to about 10 GPa, and a rate of dissolution in phosphate buffer solution from about 30 mg/min to about 60 mg/min.

Figure 9:
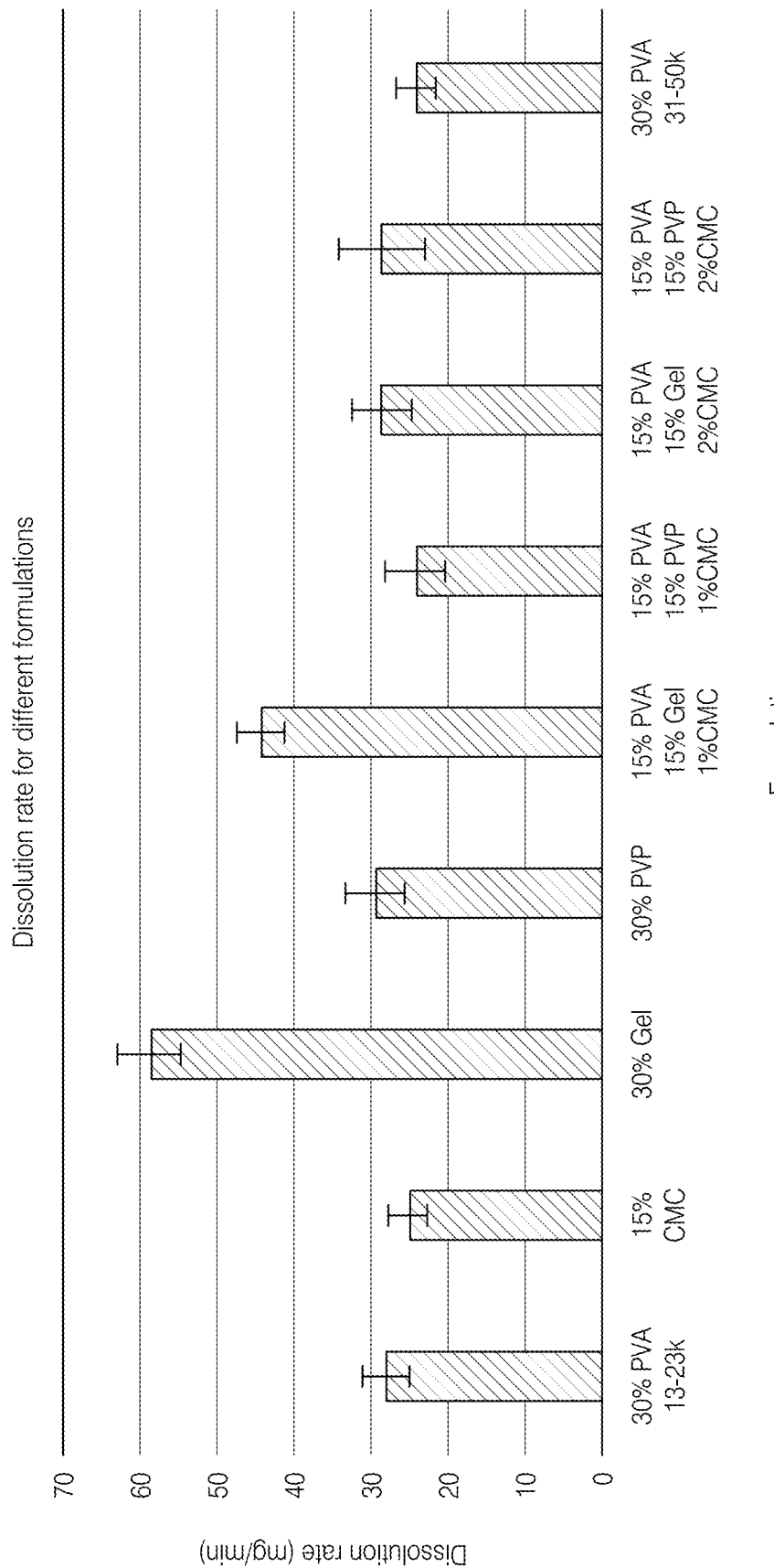
FIG. 9 is a graph of dissolution rate in phosphate buffer solution for different materials and formulations under constant agitation.

To determine the time the polymer would take to dissolve inside the body and to compare the dissolution rates of different materials, the dissolution rate of the various materials was studied. Results are shown in FIG. 9. This test was done by dissolving a dog-bone of known weight in phosphate buffer solution under constant agitation and noting the time at which the dog-bone completely dissolved out. All the materials seem to dissolve under minutes. However, it is estimated that in-vivo the materials will take longer to dissolve out because of lack of agitation and relatively low fluid content.

Figure 10:
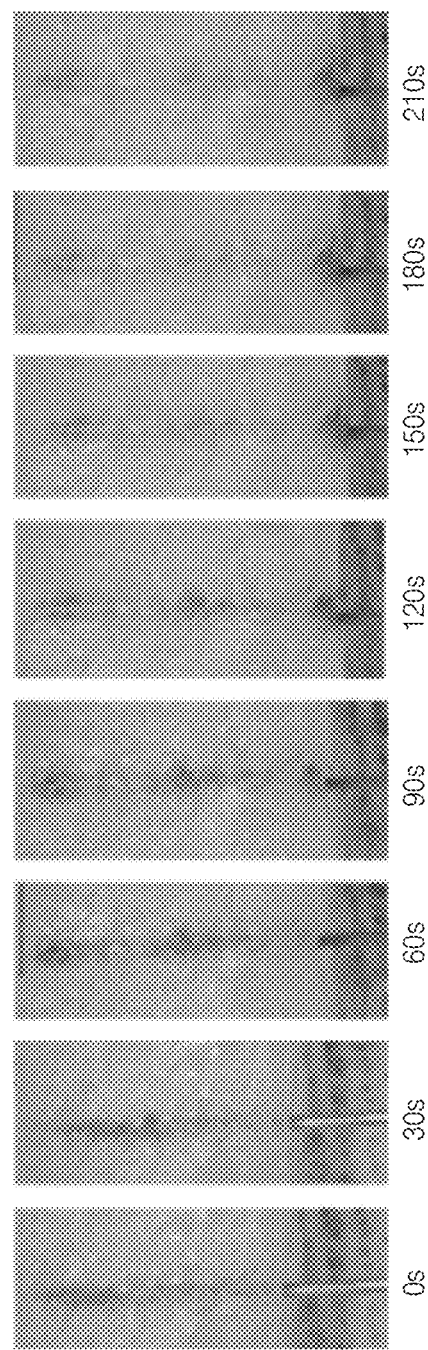
FIG. 10 contains photographs of dissolution rate for a dissolvable material disclosed herein. Below the graph are photographs of the material at time intervals corresponding to the data points on the graph. At 210 seconds, the material was completely dissolved.

Dissolution of the tip on the sensor wires was also observed through clear Syndaver to get a better idea of dissolution times in-vivo. It is estimated that the coating will dissolve within 2-3 min of insertion (FIG. 10).

Example 2: Tip/Sheath Application

The dissolvable material can be applied to the sensor tip and/or sheath by either a molding or a dip-coating process. For the molding process, the formulation to make the tip/sheath is cast in a mold, e.g., of PDMS. The sensor wire is aligned to fit the same mold. Alternatively, the sensor wire is aligned to fit in the mold and the formulation to make the tip/sheath is used to fill the mold. The formulation attaches to the tip and the wire as it dries forming a dissolvable tip or sheath.

Figure 11:
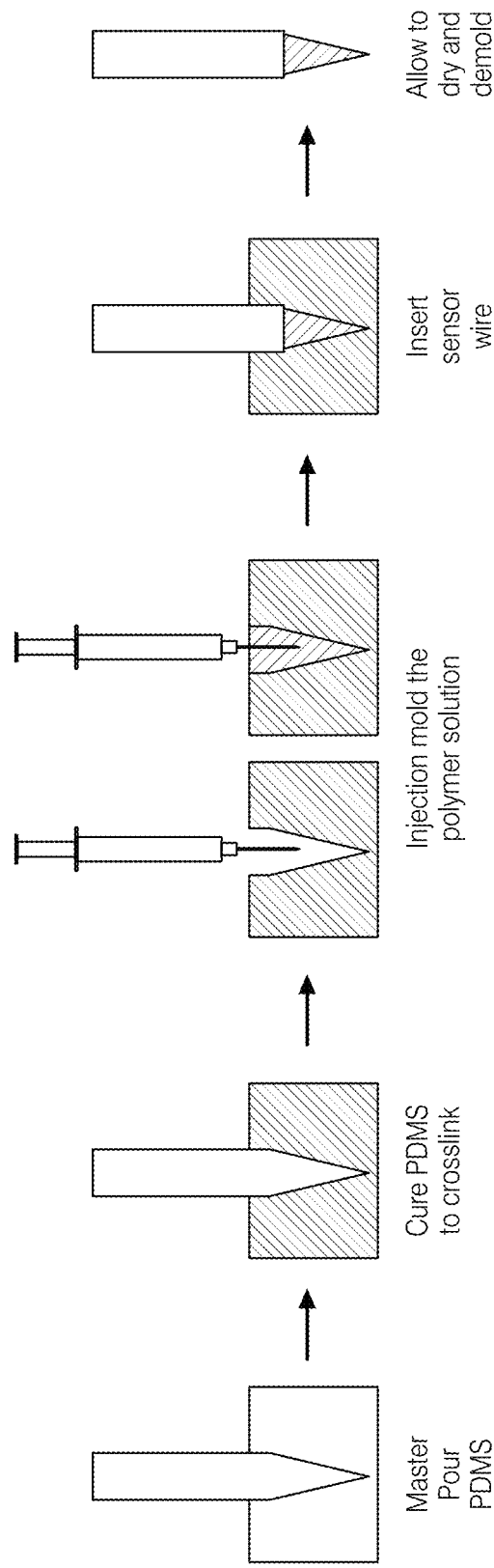
FIG. 11 is a schematic showing a generalized fabrication process for molding tips on sensor wires.

In specific examples, a mold was made by molding the shape of a sharp tipped wire using PDMS. Sylgard 184 silicone and crosslinker were mixed in 10:1 ratio and poured into a trough. The master wire tips were aligned over the trough and the PDMS was cured for 1 h at 60° C. After curing, the PDMS was peeled off to form the molds. FIG. 11, steps A and B show this step.

Next, polyvinyl alcohol (PVA), polyvinylpyrrolidone (PVP), gelatin from cold water fish skin (Gel), and Carboxy methyl cellulose (CMC) were combined in the following ratios: 15% PVA, 15% Gel, 2% CMC or 15% PVA, 15% PVP, 1% CMC. The solids were weighed out and dissolved in water at 80° C. for 1 h.

Each formulation was filled into the mold via injection molding. The wire on which the tip is to be attached was inserted into the mold and allowed to stand overnight as the formulation dries. Once dried, the wire can be demolded and the tip gets demolded along with it (FIG. 11, steps C through E).

Figure 12:
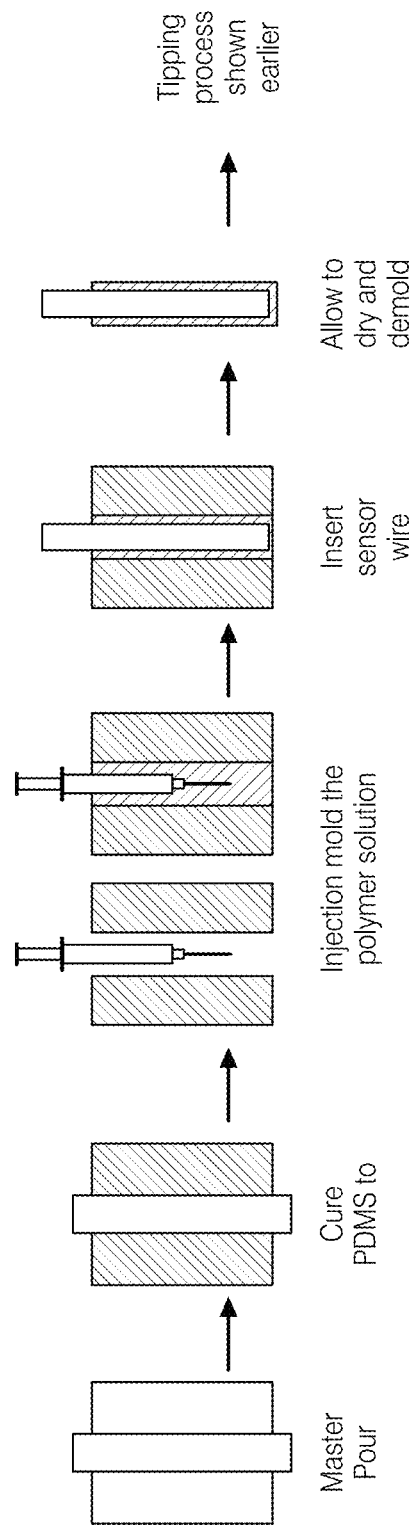
FIG. 12 is a schematic showing a generalized fabrication process for molding sheaths on sensor wires.

For certain sensors, adding a sheath can be accomplished by molding holes of about 300 µm diameter into PDMS. The holes can be filled with the formulation and the wire is inserted. The wire can be allowed to dry in the molds (e.g., overnight) and demolded after drying. This can add about a 40 µm thick coat of dissolvable material around the wire. This process is shown in FIG. 12. Alternatively, the sheath can be applied by a dip-coating process where the tip and sheath are dipped in the formulation and withdrawn at a set speed and then allowed to dry.

Figure 13:
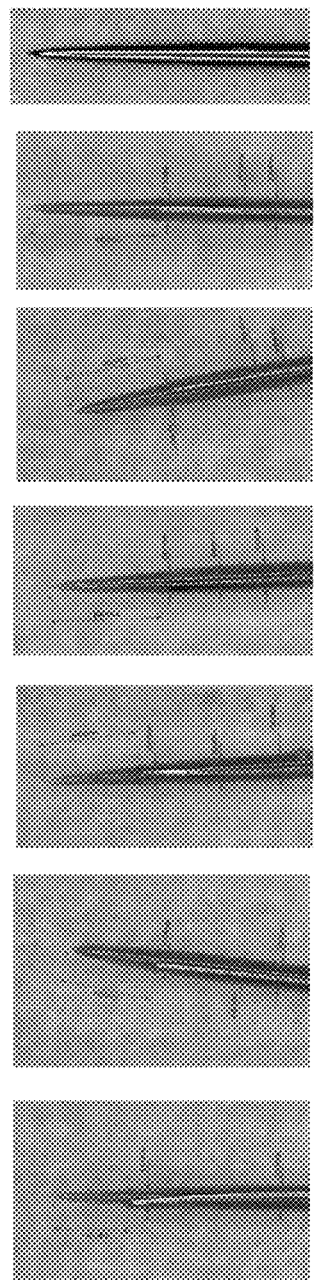
FIG. 13 is a group of images of fabricated sensor wires.
Figure 14:
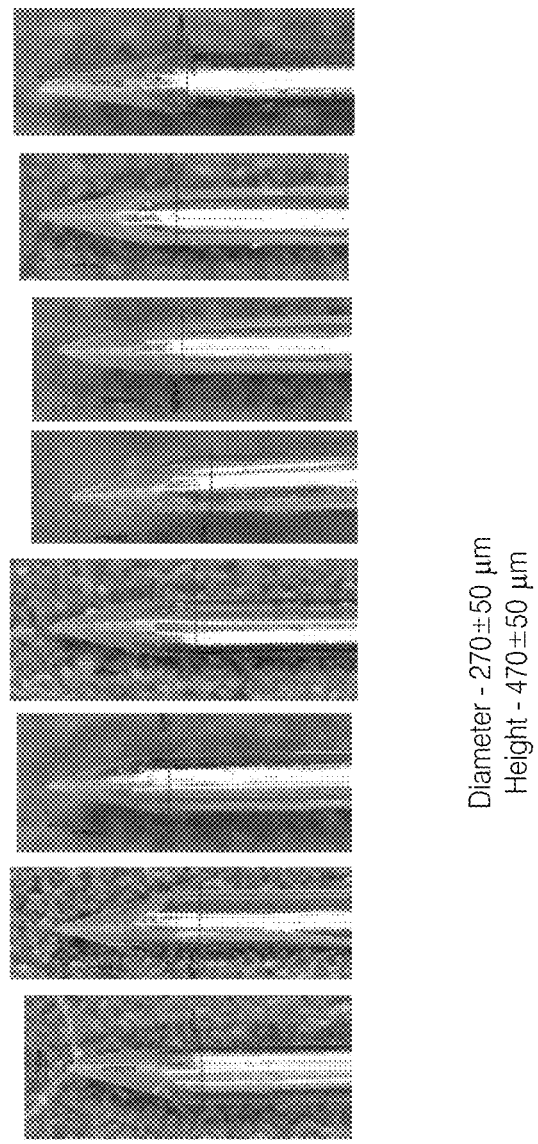
FIG. 14 shows images of fabricated tipped self-insertion sensory needles made from heavy blunted wire and tipped push rod mold.

FIG. 13 shows images of fabricated sensor wires. FIG. 14 shows images of fabricated tipped self-insertion sensory needles made from heavy blunted wire and tipped push rod mold.

Example 3: Insertion Force Measurements

The coated wires were inserted into 20N Syndaver. It is seen that the wires insert into 20N Syndaver without buckling or bending.

Figure 15:
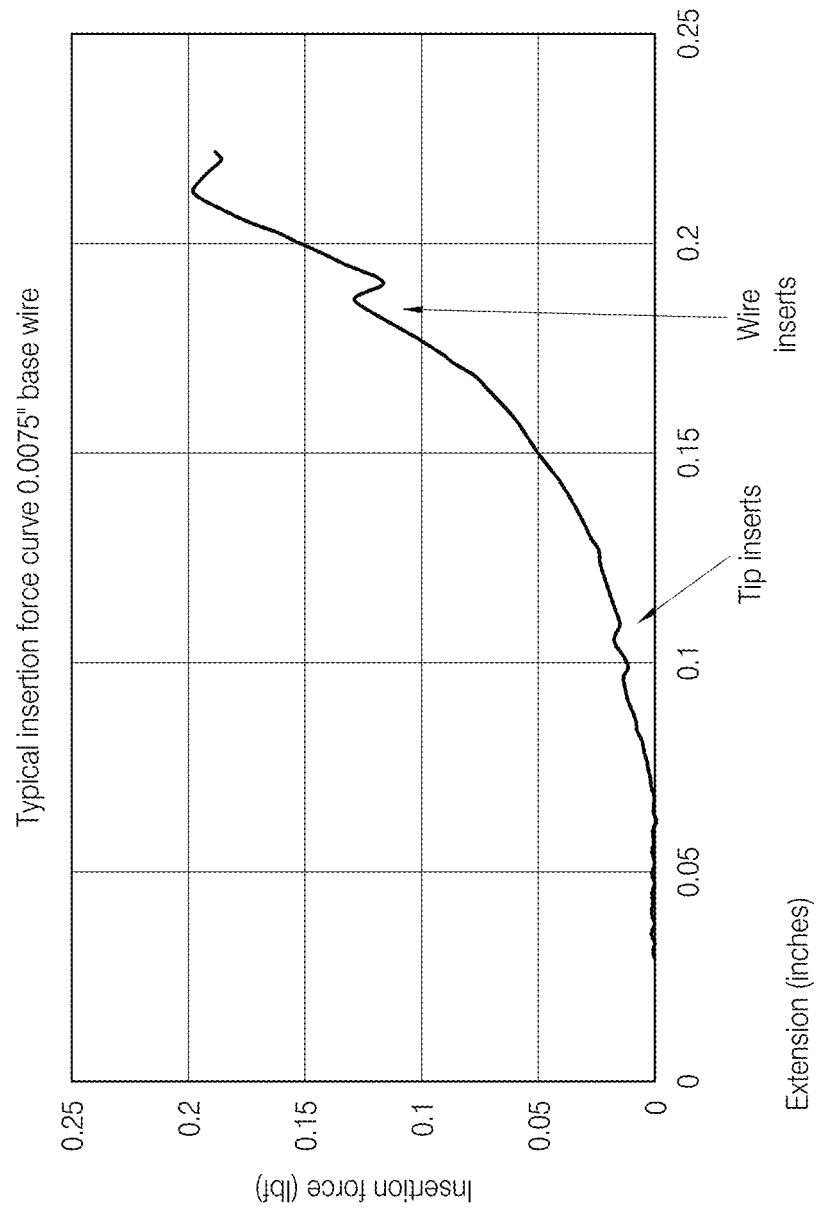
FIG. 15 is a graph showing the typical insertion force curve for a 0.0075" tack wire. The tip (PVA+CMC) inserts at a lower force than the wire.
Figure 16:
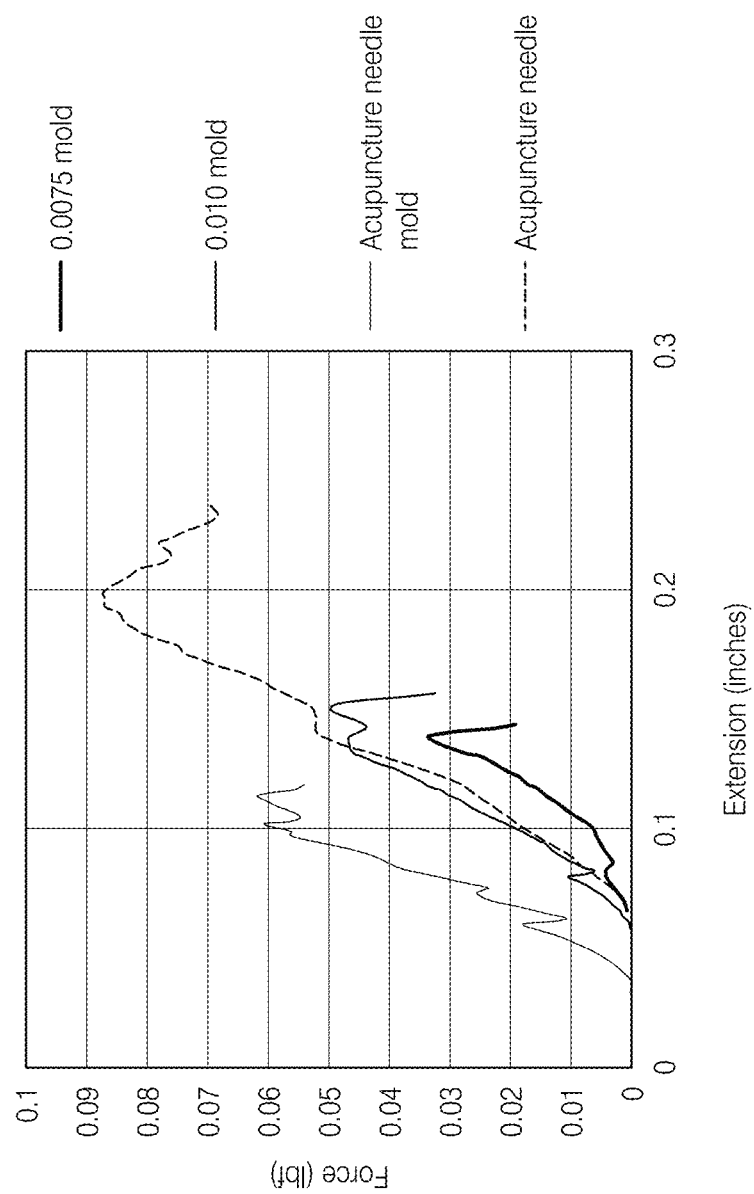
FIG. 16 is a graph showing the insertion forces for a coated tipped wire (PVA+CMC) molded with 0.0075", 0.010", and Acupuncture needle mold compared to Acupuncture needle insertion force.
Figure 17:
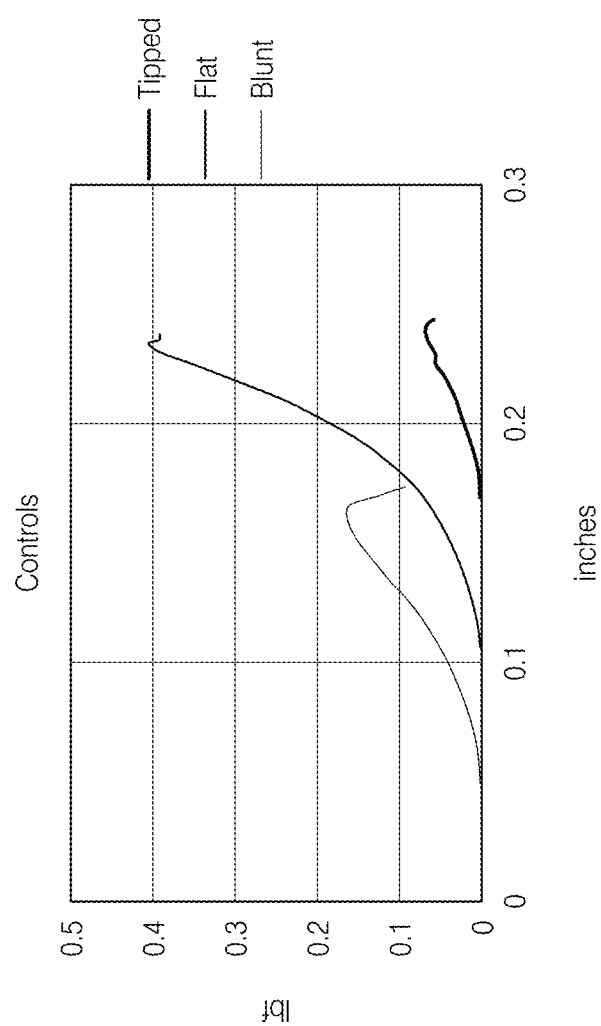
FIG. 17 is a graph showing the insertion force for self-insertion sensory needle controls.

The typical insertion profile of a tack 0.0075" wire and a uncoated wire is shown in FIGS. 15 and 16. As seen in FIG. 15, there are two distinct peaks for insertion of wire and insertion of tip. These steps in insertion force show a gradual deformation of skin during insertion. FIG. 16 shows insertion forces for uncoated wires. It is seen that the peak insertion force as well as the nature of the insertion force curve is similar to the insertion of a regular acupuncture needle. FIG. 17 shows the insertion force of various self-insertion sensory needle controls.

Figure 18:
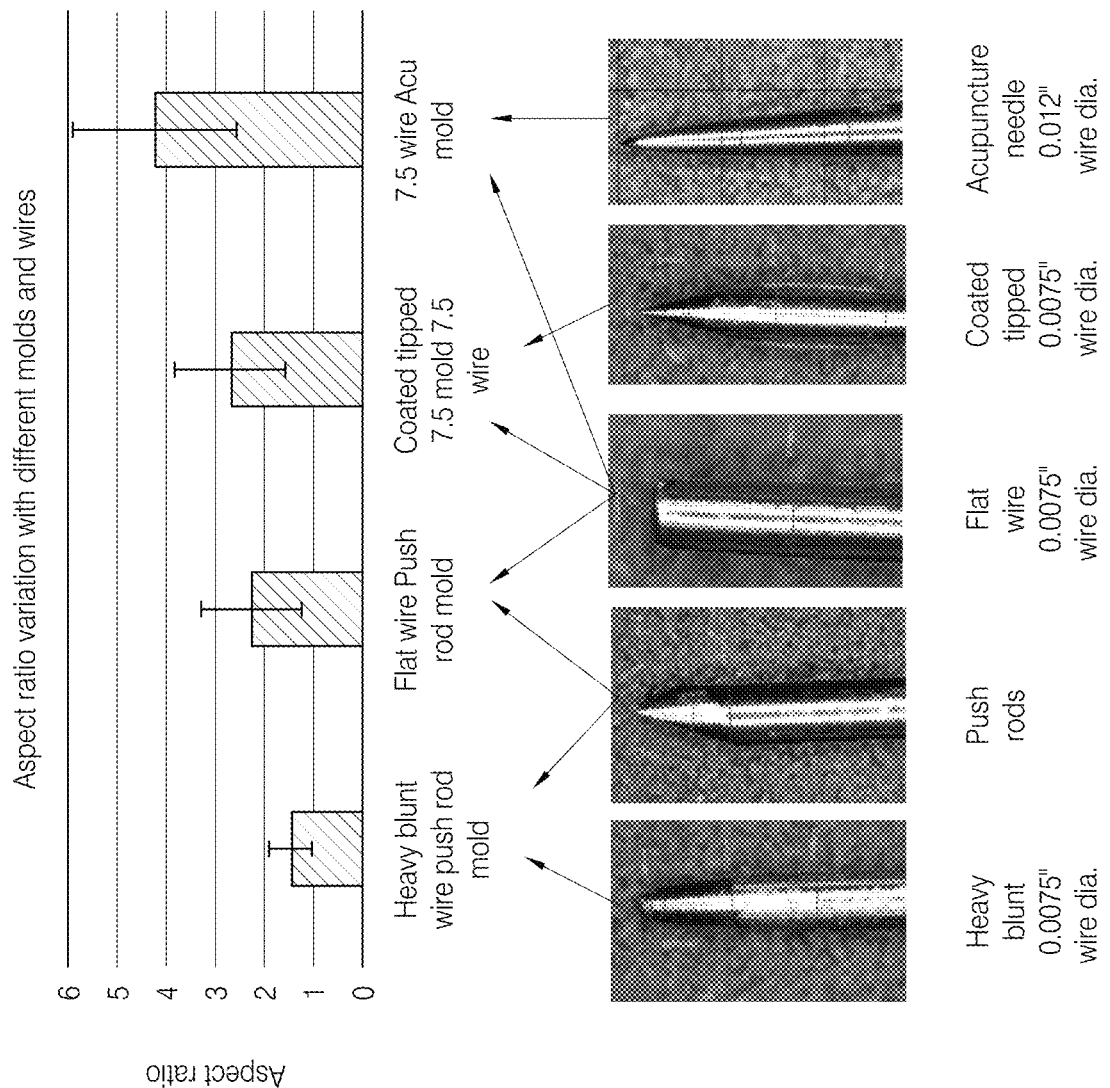
FIG. 18 shows the variation of aspect ratios arising out of different mold master and wire shapes and diameters.

Different molds and wires were tested, the resulting aspect ratios of the tips are shown in FIG. 18.

Figure 19A:
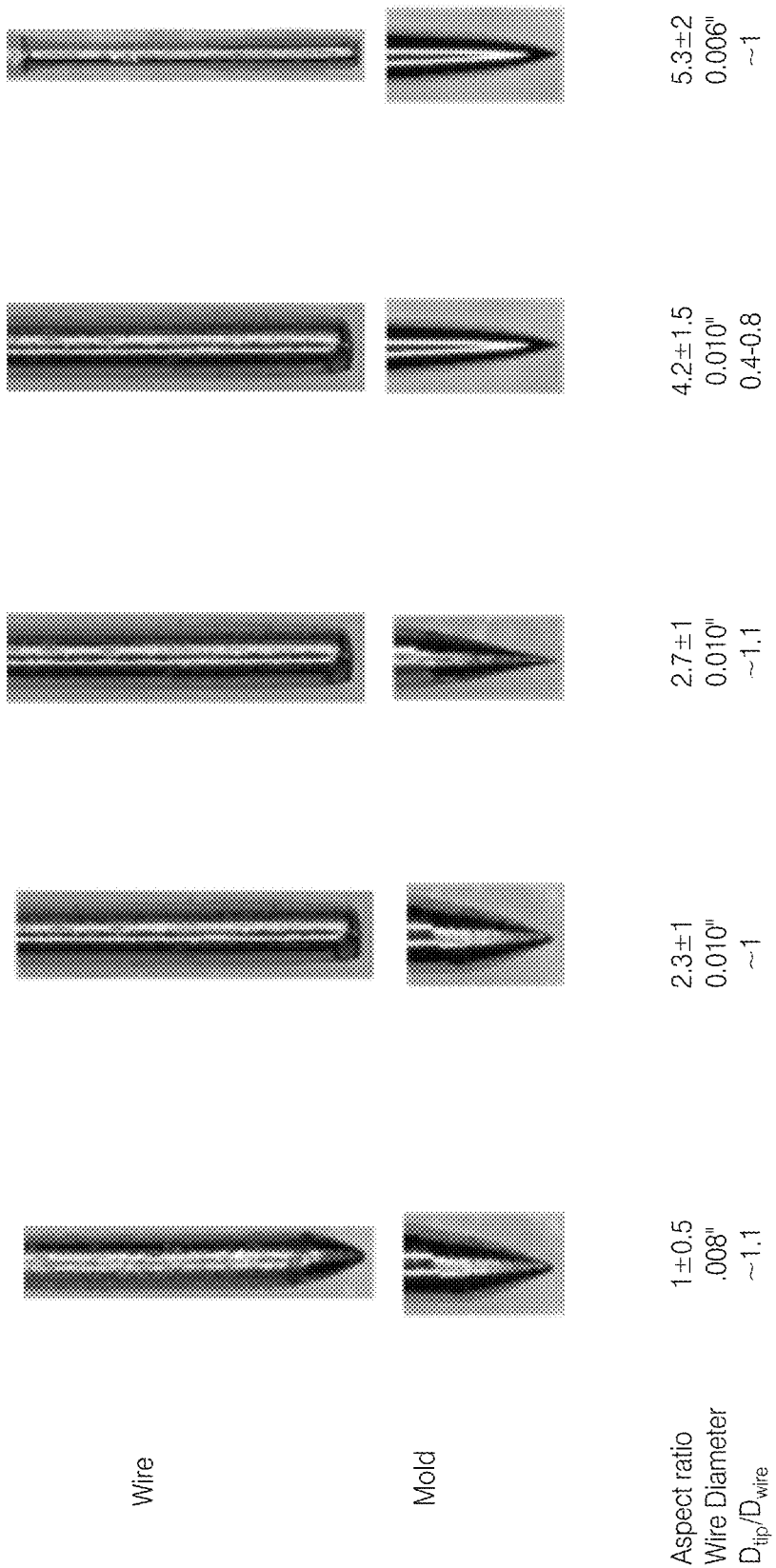
FIG. 19A illustrates different wire shapes with varying diameters and aspect ratios.
Figure 19B:
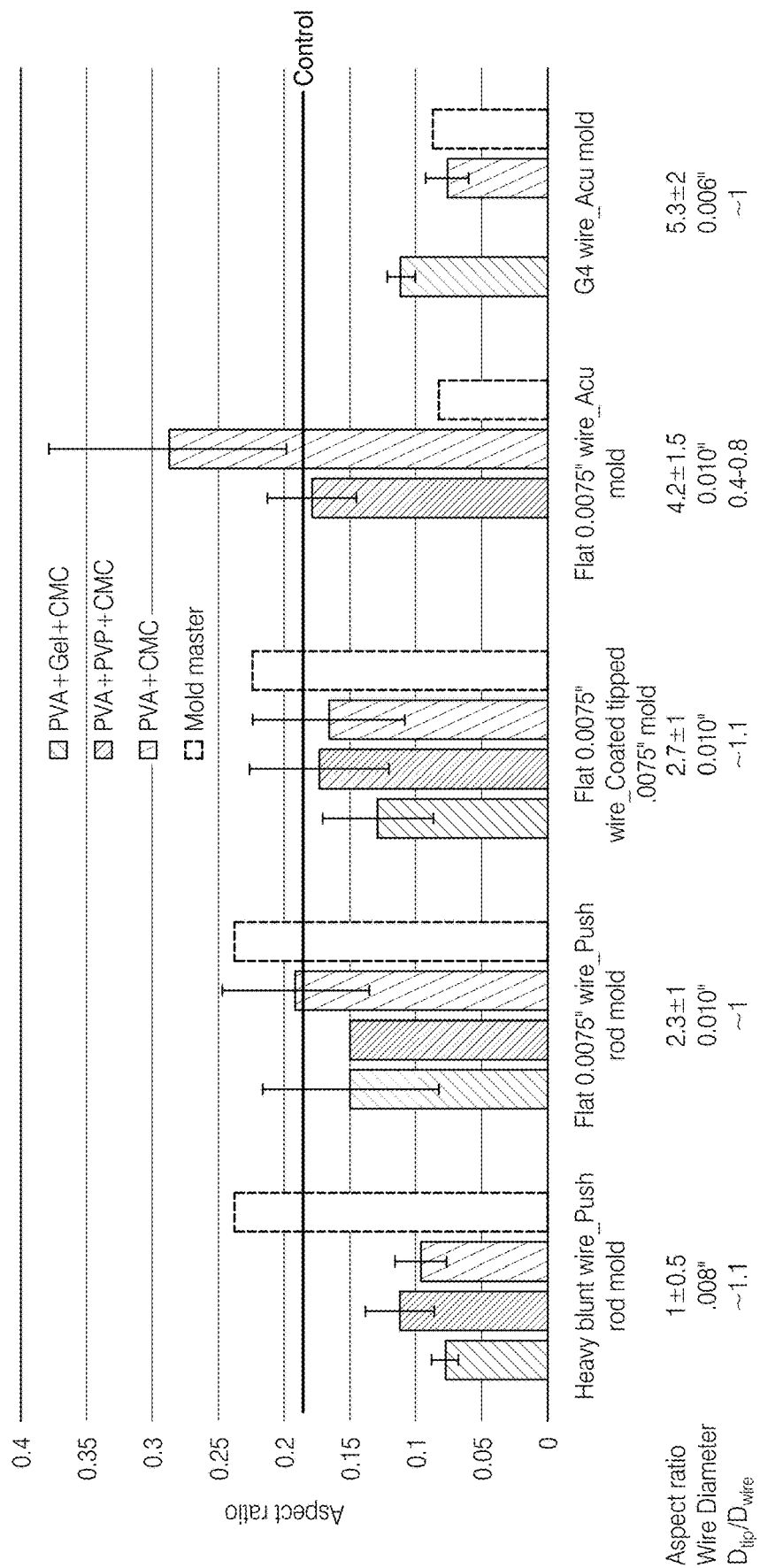
FIG. 19B is a graph of insertion forces for the wire shapes illustrated in FIG. 19A, with various combinations of mold master and wire for different material combinations.

FIG. 19A illustrates different wire shapes with varying diameters and aspect ratios. The range of insertion forces observed for the wire shapes illustrated in FIG. 19A is shown in FIG. 19B. This combines insertion forces observed in all successful insertions into 20N Syndaver. The X axis shows the combination of mold and wire used. The different bars stand for different materials.

From FIG. 19B, it was observed that insertion force is lower or equivalent to the control (insertion force of the master sharp tipped wire) for most cases except for #4 scenario when a 0.0075" wire is cast in an Acupuncture needle mold. On inspection of images and videos, this is believed to be because the ratio of diameter of base of tip to diameter of base of wire (at the junction of tip and wire) is much lower in that case. Thus, the tip inserts at a low insertion force but because of a large step in the diameters at the junction, the wire has to cut into extra skin surface area to insert. Hence, the insertion force of the wire is much higher. It is also seen that insertion force increases with increasing aspect ratio (decreasing contact angle).

Figure 20:
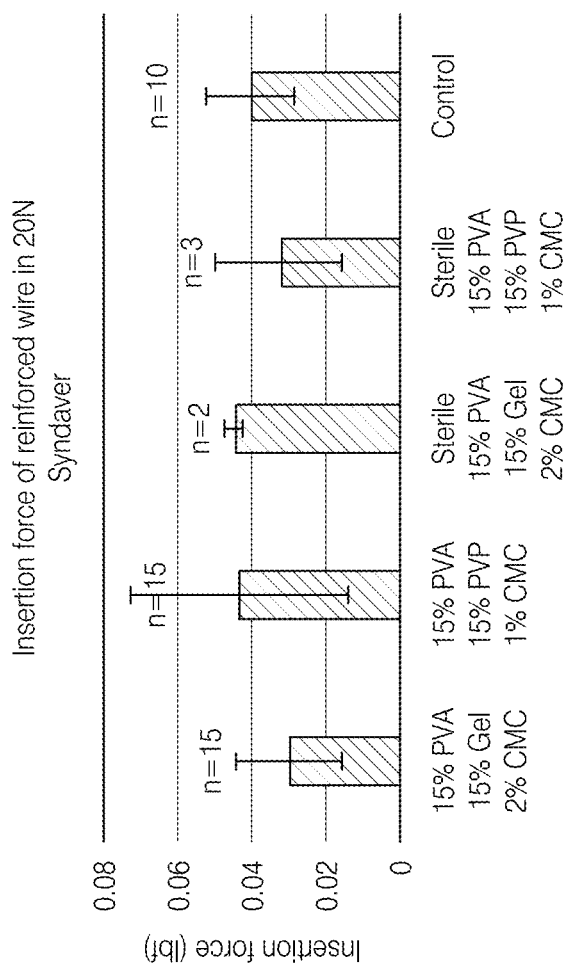
FIG. 20 is a graph of insertion forces for various combinations of reinforced commercially available needle guided glucose sensor wires.
Figure 21:
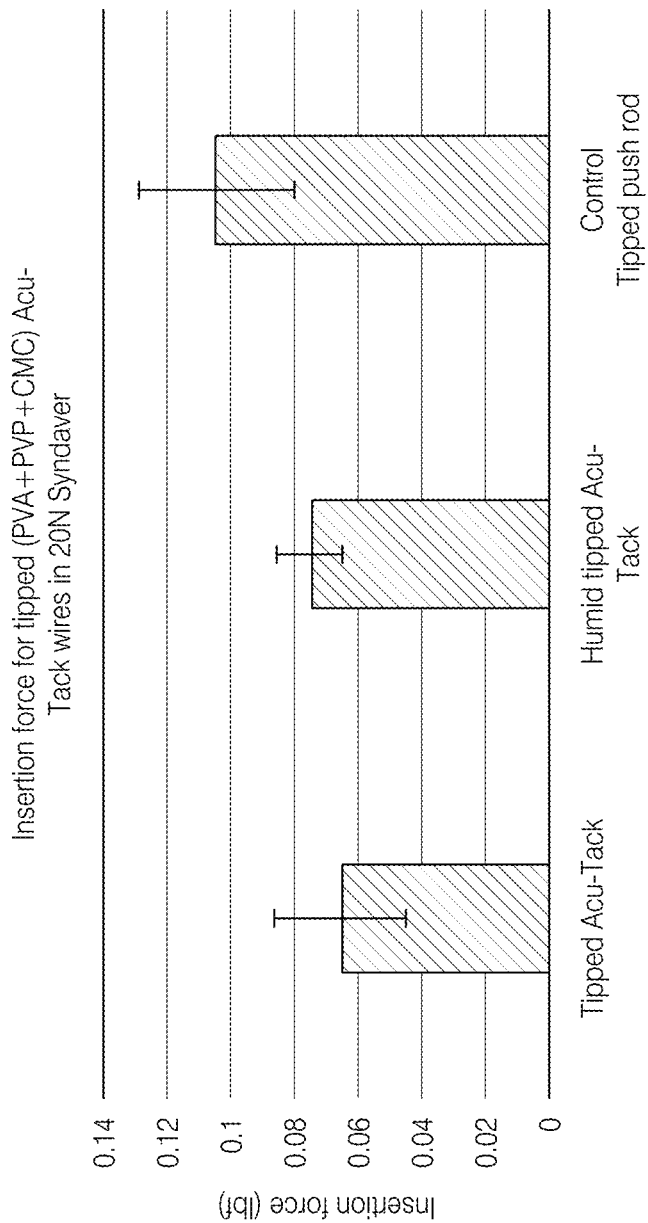
FIG. 21 is a graph of insertion force of tipped self-insertion sensory needles under ambient and humid conditions compared to control (tipped push rod).

The insertion forces of commercially available needle guided glucose sensor wires reinforced with various materials are shown in FIG. 20. The insertion forces of reinforced commercially available needle guided glucose sensor wires are much lower than that of the commercially available needle guided glucose sensor needle. They are similar to insertion force of the acupuncture needle (control). Sterilization of these wires seems to not have an impact on insertion force.

Figure 22:
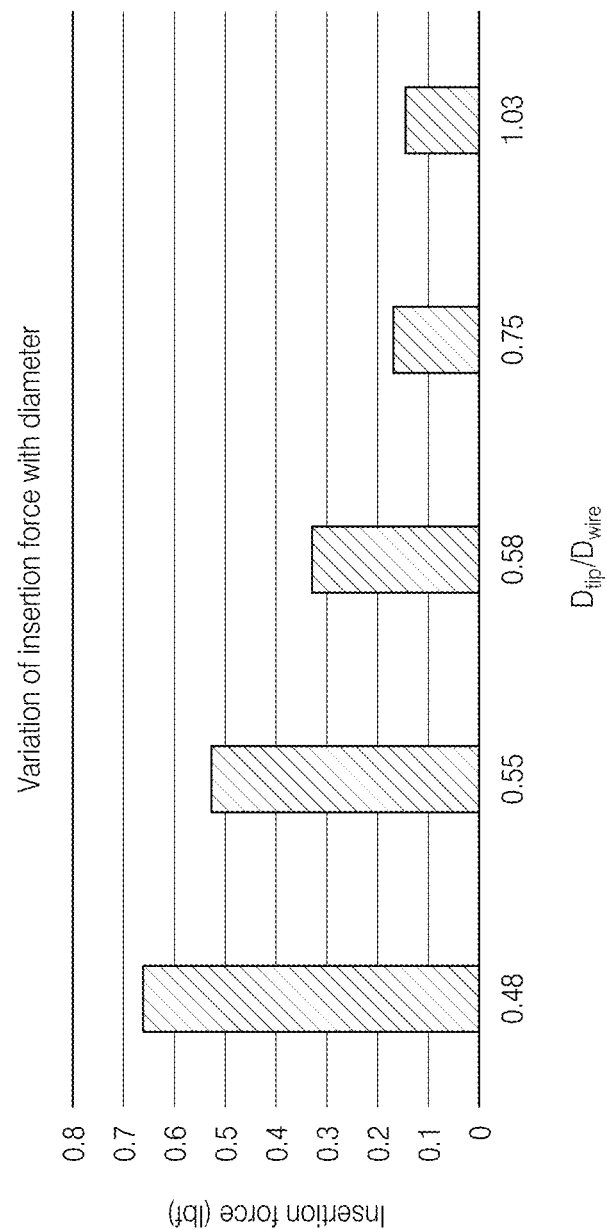
FIG. 22 is a graph showing the variation of insertion force with ratio of tip diameter to wire base diameter. PVA-CMC tips on 0.0075" wires.

From FIG. 22, it is seen that insertion force is a function of ratio of diameter of tip to diameter of wire. It can be concluded that for a feasible design, the tip needs to conform to the wire base and the diameter of the tip should be within 50% of the wire base diameter.

Example 4: Sensor Characterization

Figure 23:
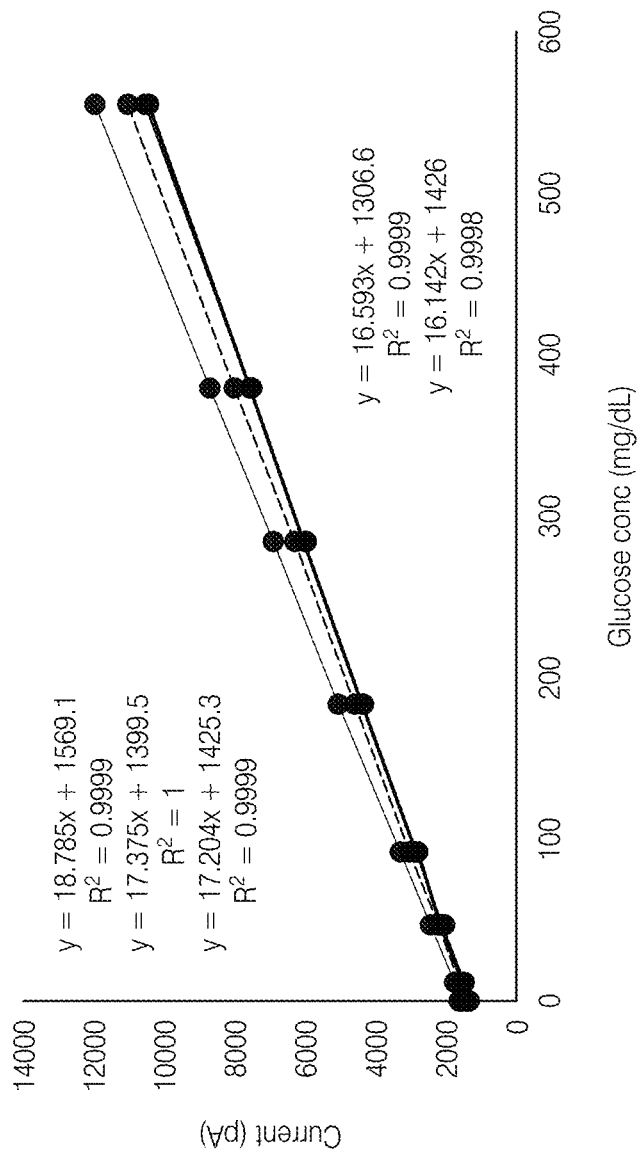
FIG. 23 is a graph of sensor output with glucose steps showing linear behavior post molding for commercially available needle guided glucose sensor wires.

To ensure that the coating does not affect the function of the sensor, linearity of sensor was tested by applying glucose steps. Each series in FIG. 23 represents an individual commercially available needle guided glucose sensor coated and tipped with PVA and CMC made using the same processing conditions. The sensors were inserted into 20N Syndaver. The polymer coating was dissolved out and the glucose steps were done to test for linearity. The sensor response was found to be linear as seen in FIG. 23.

Figure 24:
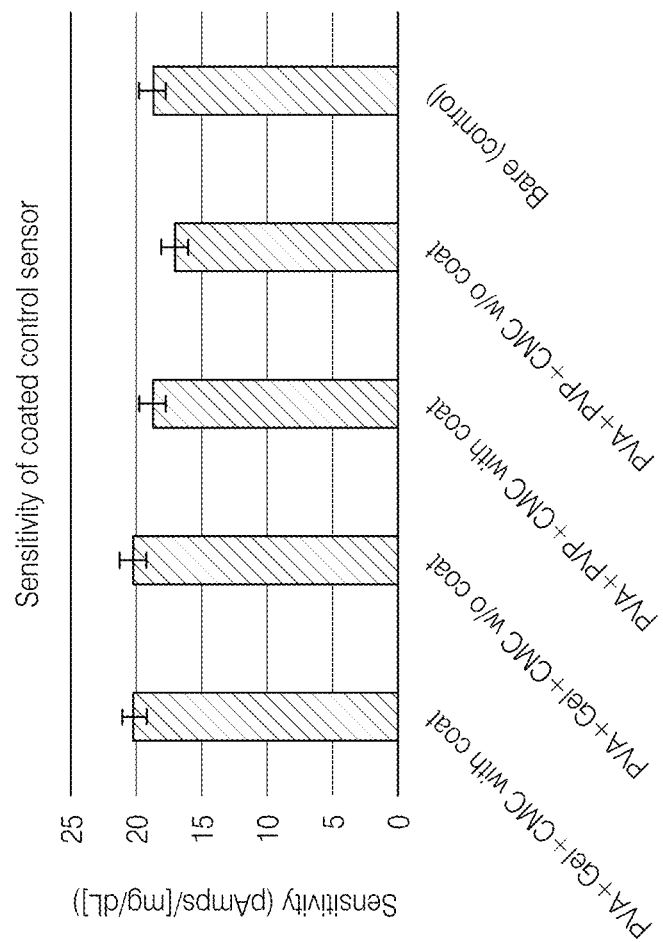
FIG. 24 is a graph showing the initial sensitivity of the sensor for commercially available needle guided glucose sensor wires coated with PVA, PVP, Gel and CMC.
Figure 25:
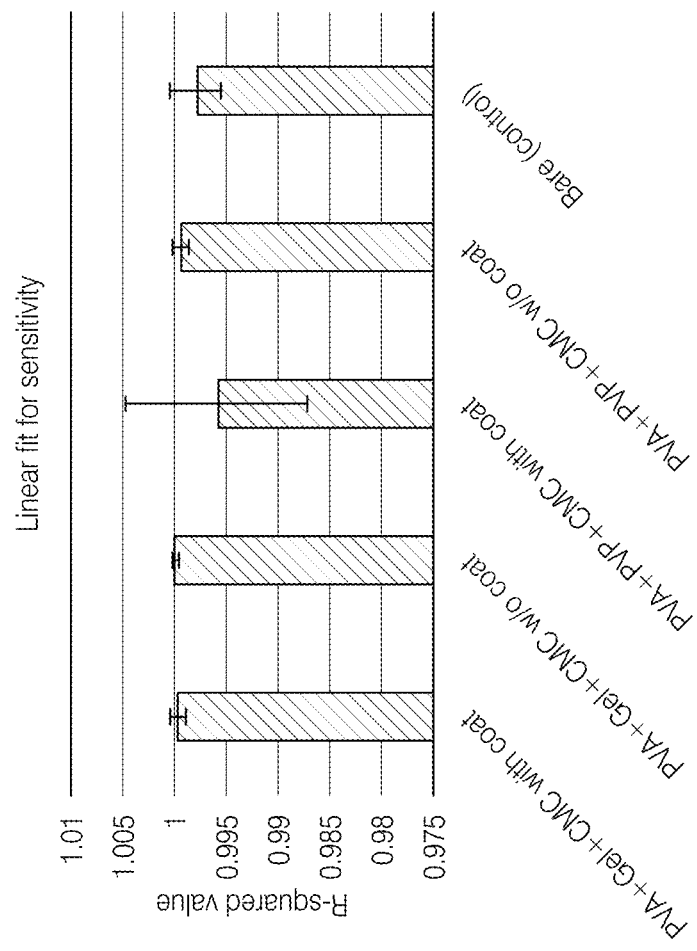
FIG. 25 is a graph showing the R-squared value showing the fit for sensitivity with steps of glucose concentration.

Commercially available needle guided glucose sensors coated with PVA, PVP, CMC and PVA, Gel, CMC were also tested for retention of sensitivity post-fabrication. The initial function was found to be linear and similar to controls, as seen in FIGS. 24 and 25.

Example 5: Buckling Measurements

Since commercially available needle guided glucose sensor is the thinnest wire and buckles easily, it was of interest to see if molding the dissolvable material along the shaft would increase the buckling strength and also whether this increase in buckling strength is enough to survive the insertion force.

Buckling force measurements (one end free) are done by clamping the commercially available needle guided glucose sensor wire on one end leaving 5 mm free length. The wire is then pushed down on a substrate on which it can slip. The buckling force is measured using a load cell on an Instron. The table shows that tipped commercially available needle guided glucose sensor wire coated partially along the shaft increases buckling force (one end free).

TABLE 1

| Commercially available needle guided glucose sensor wire coat | Buckling force (lbf) | Thickness |
| --- | --- | --- |
| Bare commercially available needle guided glucose sensor wire | 0.038 | 161 μm |
| 30% PVA + 1% CMC | 0.049 | 204 μm |
| 30% PVA + 3% CMC | 0.052 | 216 μm |
| 15% PVA, 15% PVP, 2% CMC | 0.058 | 222 μm |
| 15% PVA, 15% Gel, 2% CMC | 0.077 | 210 μm |

These data indicate that the buckling force increases on reinforcement and the buckling force increase is dependent on the coated material.

Figure 26:
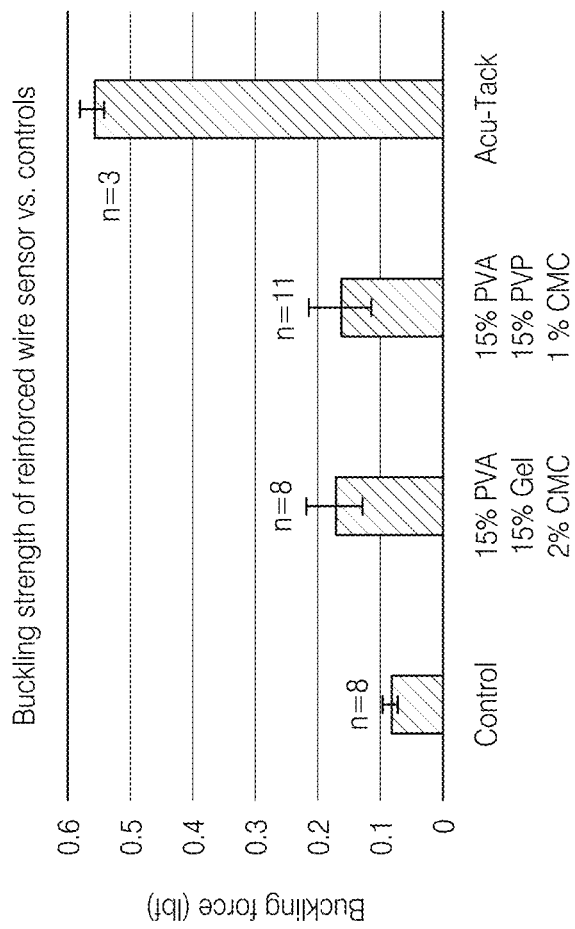
FIG. 26 is a graph showing the buckling force for reinforced commercially available needle guided glucose sensor wires coated with PVA+Gel+CMC/PVA+PVP+CMC.

A commercially available needle guided glucose sensor wire shaft was coated all the way with various materials to test for reinforcement and buckling strength. To replicate a scenario similar to skin insertion where both ends are fixed, one end is fixed on a champ and the other end is fixed on a non-slipping surface leaving 5 mm free length. From FIG. 26, reinforcing commercially available needle guided glucose sensor wire all along the shaft is shown to increase buckling force (both ends fixed) by approximately 100% (FIG. 26).

Since, the insertion force observed for commercially available needle guided glucose sensor insertion is less than 0.15 lbf for all successful insertions, it can be concluded that this reinforcement (~50 μm thickness) is sufficient for self-insertion of commercially available needle guided glucose sensor wire.

Example 6: Sterilization and Humidity Cycling

Figure 27:
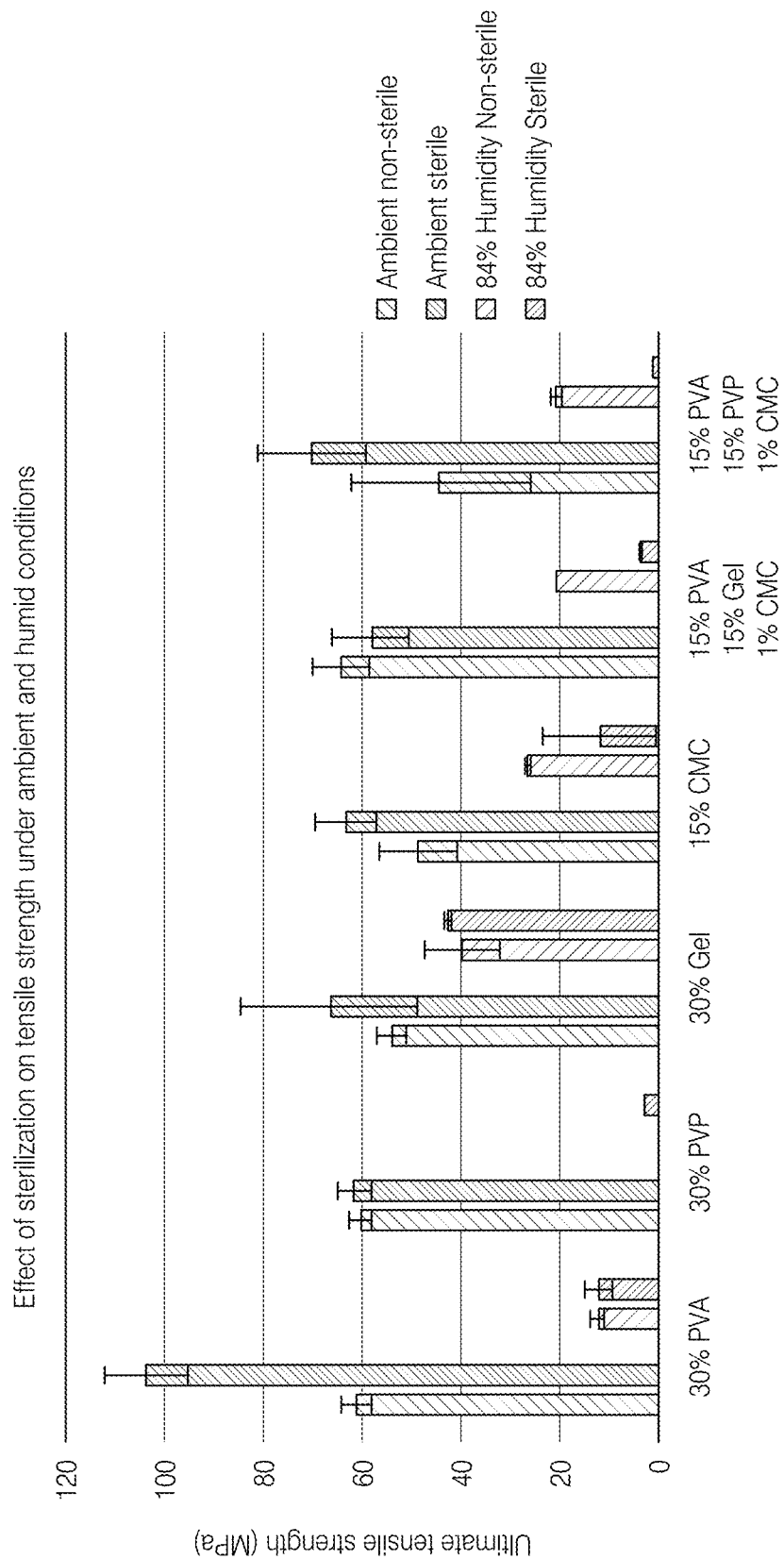
FIG. 27 is a graph showing the effect of sterilization on tensile strength for various compositions.
Figure 28:
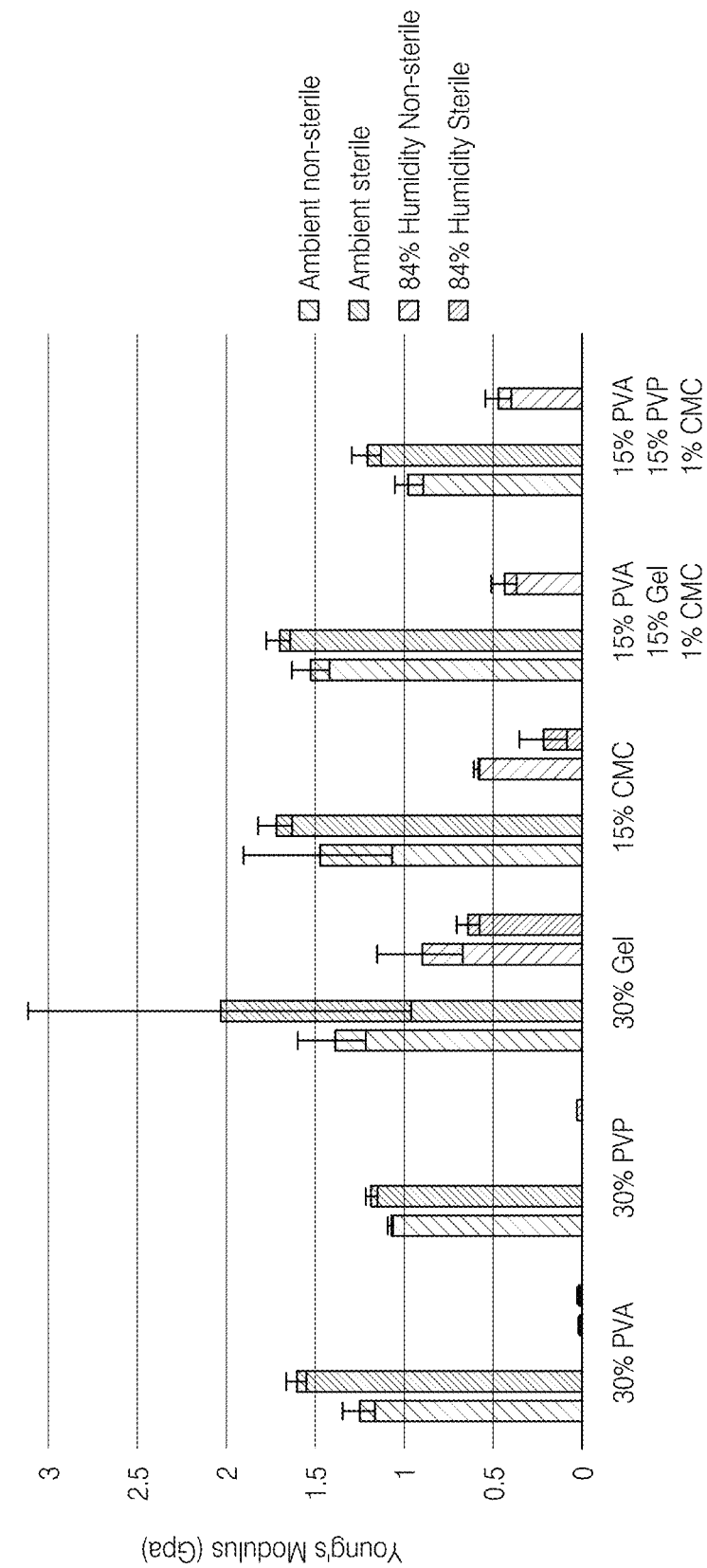
FIG. 28 is a graph showing the effect of sterilization on Young's modulus for various compositions.

Films were sterilized at 25-35 GKy. Tensile testing was done on the films under ambient and humid conditions. The data shows a significant change in the tensile stress properties for PVA but relatively does not affect other materials. It is hypothesized that PVA forms physical crosslinks because of radiation. FIG. 27 and FIG. 28.

Figure 29A:
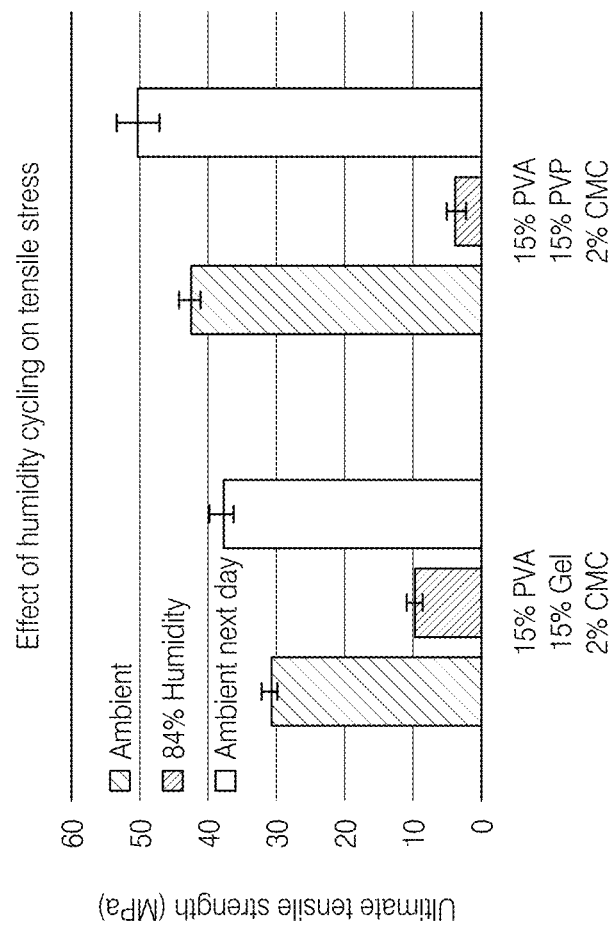
FIGS. 29A and 29B are a pair of graphs showing the effect of pF humidity cycling on tensile strength and Young's modulus of various compositions.
Figure 29B:
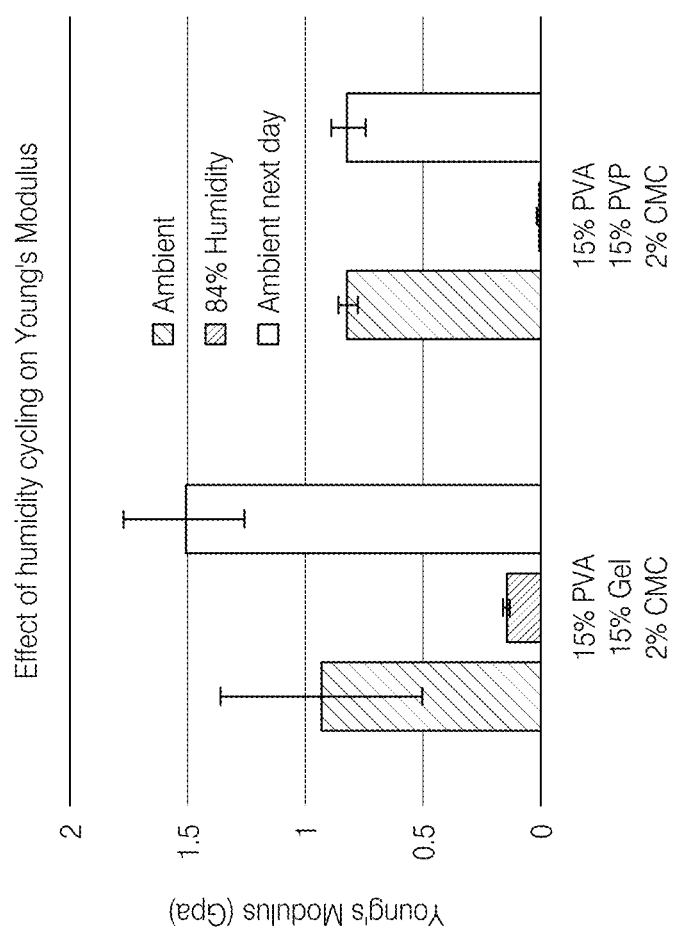

Films were subjected to cycles of humidity to estimate whether subjecting the material to humid followed by ambient conditions makes the material regain strength and stiffness. Results from tensile testing are shown in FIGS. 29A and 29B. It can be concluded that the material does regain strength and retain shape on going from humid to ambient conditions.

Methods and devices that are suitable for use in conjunction with aspects of the preferred embodiments are disclosed in U.S. Pat. Nos. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206, 297; 8,216,139; 8,229,534; 8,229,535; 8,229,536; 8,231, 531; 8,233,958; 8,233,959; 8,249,684; 8,251,906; 8,255, 030; 8,255,032; 8,255,033; 8,257,259; 8,260,393; 8,265, 725; 8,275,437; 8,275,438; 8,277,713; 8,280,475; 8,282, 549; 8,282,550; 8,285,354; 8,287,453; 8,290,559; 8,290, 560; 8,290,561; 8,290,562; 8,292,810; 8,298,142; 8,311, 749; 8,313,434; 8,321,149; 8,332,008; 8,346,338; 8,364, 229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0176136-A1; U.S. Patent Publication No. 2005-0182451-A1; U.S. Patent Publication No. 2005-0245799-A1; U.S. Patent Publication No. 2005-0033132-A1; U.S. Patent Publication No. 2005-0051427-A1; U.S. Patent Publication No. 2005-0056552-A1; U.S. Patent Publication No. 2005-0090607-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0331644 A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-

0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2013-0053665-A1; U.S. Patent Publication No. 2013-0053666-A1; US. Patent Publication No. 2013-0060112-A1; US. Patent Publication No. 2013-0078912-A1; US. Patent Publication No. 2013-0076531-A1; US. Patent Publication No. 2013-0076532-A1; US. Patent Publication No. 2013-0131478-A1; US. Patent Publication No. 2013-150692-A1; U.S. Patent Publication No. 2014-0094671-A1; US. Patent Publication No. 2014-0005508-A1; US. Patent Publication No. 2014-0118166-A1; US. Patent Publication No. 2014-0118138-A1; US. Patent Publication No. 2014-0188402-A1; US. Patent Publication No. 2014-0182350-A1; and US. Patent Publication No. 2014-0275896-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS," and U.S. application Ser. No. 13/461,625 filed on May 1, 2012 and entitled "DUAL ELECTRODE SYSTEM FOR A CONTINUOUS ANALYTE SENSOR."

This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

The term "host" as used herein is a broad term, and is to be given its ordinary and customary meaning to a person of ordinary skill in the art (and is not to be limited to a special or customized meaning), and refers without limitation to animals (e.g., humans) and plants. In some examples, a host can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. In other examples, a host can include a mammal, such as a primate or a human.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A system for measuring an analyte concentration, the system comprising:
   a sensor comprising at least one electrode, and a membrane covering at least a portion of the at least one electrode; and
   a tissue-piercing element comprising a dissolvable material that dissolves after insertion into a host, the tissue-piercing element configured to pierce tissue of the host, wherein the dissolvable material has a tensile strength of from about 20 MPa to about 90 MPa as measured by ASTM-D2370.

2. The system of claim 1, wherein the sensor includes a sensor body coated with a sheath comprising the dissolvable material or a different dissolvable material.

3. The system of claim 2, further comprising:
   a mounting unit, wherein the tissue-piercing element extends past the sensor body in the direction of the mounting unit, but stops short of the at least one electrode.

4. The system of claim 2, wherein the sheath comprises the different dissolvable material than in the tissue-piercing element.

5. The system of claim 2, wherein at least one of the dissolvable material and the different dissolvable material comprise an anti-inflammatory.

6. The sensor device of claim 2, wherein the tissue-piercing element has a base diameter $D_{tip}$ and the sensor body has a diameter $D_{wire}$, and the ratio $D_{tip}/D_{wire}$ is greater than 0.75.

7. The system of claim 1, wherein the dissolvable material has a rate of dissolution in phosphate buffer solution from about 20 mg/min to about 60 mg/min.

8. The system of claim 1, wherein the dissolvable material has a Young's modulus of from about 1 GPa to about 10 GPa as measured by method ASTM-D2370.

9. The system of claim 1, wherein the sensor has buckling strength of at least 0.040 lbf.

10. The system of claim 1, wherein the dissolvable material comprises polyvinylalcohol and one or more of polyvinylpyrrolidone, protein, or polysaccharide.

11. The system of claim 1, wherein the dissolvable material comprises polyvinylalcohol and gelatin.

12. The system of claim 1, wherein the dissolvable material comprises a protein at a weight percentage of about 46 wt. % or more based on the total weight of the dissolvable material.

13. The system of claim 1, wherein the dissolvable material comprises a polysaccharide at a weight percentage from about 2 wt. % to about 10 wt. % based on the total weight of the dissolvable material.

14. The system of claim 13, wherein the polysaccharide is carboxymethylcellulose.

15. The system of claim 1, wherein the dissolvable material comprises from about 46 wt. % to about 49 wt. % polyvinylalcohol from about 46 wt. % to about 49 wt. % gelatin, and from about 2 wt. % to about 8 wt. % carboxymethylcellulose.

16. The system of claim 1, wherein the dissolvable material comprises from about 91 wt. % to about 97 wt. % polyvinylalcohol and from about 3 wt. % to about 9 wt. % carboxymethylcellulose.

17. The system of claim 1, wherein the dissolvable material further comprises one or more materials configured to suppress wounding, to promote rapid wound healing, to induce osmotic pressure or oncotic pressure, or a combination thereof.

18. The system of claim 1, wherein the dissolvable material further comprises one or more drugs.

19. The system of claim 18, wherein the one or more drugs comprises dexamethasone.

20. A system for measuring an analyte concentration, the system comprising:
   a sensor comprising at least one electrode, and a membrane covering at least a portion of the at least one electrode; and
   a tissue-piercing element comprising a dissolvable material that dissolves after insertion into a host, the tissue-piercing element configured to pierce tissue of the host, wherein the dissolvable material has a Young's modulus of from about 1 GPa to about 10 GPa as measured by ASTM-D2370.

* * * * *